(12) United States Patent
Kondo et al.

(10) Patent No.: US 6,628,978 B1
(45) Date of Patent: Sep. 30, 2003

(54) BIOMAGNETISM MEASUREMENT DEVICE AND METHOD OF BIOMAGNETISM MEASUREMENT USING THE DEVICE

(75) Inventors: Shoji Kondo, Hitachinaka (JP); Hitoshi Sasabuchi, Mito (JP); Hiroyuki Suzuki, Hitachinaka (JP); Keiji Tsukada, Kashiwa (JP); Akihiko Kandori, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/424,622

(22) PCT Filed: Mar. 16, 1999

(86) PCT No.: PCT/JP99/01561

§ 371 (c)(1),
(2), (4) Date: Nov. 24, 1999

(87) PCT Pub. No.: WO99/49781

PCT Pub. Date: Oct. 7, 1999

(30) Foreign Application Priority Data

Mar. 27, 1998 (JP) ............................................. 10-081260
Jul. 22, 1998 (JP) ............................................. 10-206175

(51) Int. Cl.$^7$ ................................................. A61B 5/05
(52) U.S. Cl. ........................ 600/409; 324/248; 324/261
(58) Field of Search ................................ 324/248, 261; 378/205, 206

(56) References Cited

FOREIGN PATENT DOCUMENTS

| JP | 50-96088 | 7/1975 |
|---|---|---|
| JP | 57-13006 | 1/1982 |
| JP | 2-180244 | 7/1990 |
| JP | 3-244433 | 10/1991 |
| JP | 4-109929 | 4/1992 |
| JP | 4-109930 | 4/1992 |
| JP | 8-137547 | 5/1996 |
| JP | 9-250689 | 9/1997 |

OTHER PUBLICATIONS

PTO 02–1773 translation of JP 04–109929, Ken'ji Shibata, Method for Measuring Biomagnetism.*
Romani et al, "Biomagnetic Instrumentation", Rev. Sci, Instrum., vol. 53, 1982, pp. 1815–1845.

* cited by examiner

Primary Examiner—Marvin M. Lateef
Assistant Examiner—Runa Shoh Qaderi
(74) Attorney, Agent, or Firm—Mattingly, Stanger & Malur, P.C.

(57) ABSTRACT

In the present invention, when measuring magnetism of a measuring portion of a patient by making use of a dewar incorporating magnetism sensors each including a super conducting quantum interference device, a bed is at first positioned outside a position immediately below the dewar. At this position outside the position immediately below the dewar the patient is laid on the bed in an inspection posture. Marks are attached on the body of the patient at three points for setting X and Y axis coordinate on the measurement portion, at the position outside the position immediately below the dewar cross shaped beam patterns are projected and the position of the bed is adjusted so that the marks at the three points locate on the cross shaped beam patterns, thereafter, bed is transferred by a constant amount to the position immediately below the dewar. Thereby, in the biomagnetism measurement the correlated position between the dewar (magnetism sensors) and the measurement portion of the patient can be ascertained easily and accurately.

32 Claims, 17 Drawing Sheets

BIOMAGNETISM MEASUREMENT DEVICE AND METHOD OF BIOMAGNETISM MEASUREMENT USING THE DEVICE

FIELD OF THE INVENTION

The present invention relates to a biomagnetism measurement device and a method of biomagnetism measurement which are suitable for measuring a magnetic field (for example, a magnetic field being caused by a nerve activity or myocardial activity of a heart) occurring from a portion to be measured of a living body (a patient to be inspected) by making use of a super conducting quantum interference device (hereinbelow abbreviated as SQUID) which serves as a highly sensitive magnetism sensor.

BACKGROUND ART

Since the SQUID which is developed in association with a growth of technology with regard to superconducting devices functions as a highly sensitive magnetism sensor, a technology which measures a magnetic field distribution caused by a living body making use of the SQUID and uses the same as medical diagnosis data is now being established in a medical measurement field.

FIG. 16 shows an arrangement diagram when such biomagnetism measurement device is applied for a cardio magnetism measurement system.

The cardio magnetism measurement is performed in a magnetically shielded room 1 so as not to be affected by environmental magnetic noises. A patient 2 to be inspected lies down on a bed 3, and is positioned close to and immediately below a bottom of a dewar (vessel) 4 so that a portion to be measured (a center position of a heart) meets with a center position of the dewar 4 (which includes magnetism sensors formed by integrating detection coils and the SQUIDs and is constituted by a cylindrical container filled with liquid He) supported by a gantry 5.

For He being evaporated, liquid He is continuously supplemented to a liquid He tank 6 by an automatic supply device 7 disposed outside the magnetically shielded room 1.

Outputs of the magnetism sensors are inputted to an FLL circuit 8 wherein voltage outputs proportional to the detected magnetic field intensities are obtained. The output voltages are amplified and of which frequency band are selected via an amplifier and filter circuit 9, and are taken in by a computer 10 after being A/D converted, wherein signal processing is performed and the processed data are outputted therefrom.

A dewar 4 for the biomagnetism measurement, for example, as disclosed in G. L. Romani, et al., Rev. Sci. Instrom, 53. pp. 1815–1845(1982), is configurated in a cylindrical shape or a combination of cylinders of different diameters and is disposed vertically because of easy production from its structural point of view.

Further, in a system for measuring a cardio magnetism most of the bottom faces of such cylindrical shaped dewars are configurated in flat, because a chest wall of a living body is nearly flat. In case of cardio magnetism measurement, after a patient to be inspected lay on the patient's back on the bed 3 which is constituted to be movable freely (permitted position adjustment) in backward and forward, right and left and upward and downward with respect to the dewar 4, it was necessary to meet the heart portion (center position of the heart) in the chest wall area of the patient 2 to be inspected with the center position of the bottom face of the dewar 4 and to come close thereto by adjusting respective movable portions in the bed 3.

However, if the measurement portion of the patient to be measured touches the bottom face of the dewar 4 which causes noises, therefore, it is necessary to place the measurement portion away therefrom to some extent, however, if the measurement portion is placed away excessively, the sensitivity of the sensors reduces, therefore, a positioning operation has to be repeated many times for determining an optimum position visually.

FIG. 17 shows a conventional common method of positioning a measurement portion with respect to a dewar 4.

In the conventional cardio magnetism measurement device the bed 3 for placing the patient 2 to be inspected thereon is disposed on a traveling stand 12 which is movable in back and forth direction along back and forth transferring use trails 11 via an elevation means 13 and a right and left direction moving means 14.

The traveling stand 12 is either manually driven or electrically driven by a motor, and moves in the back and forth direction on the back and forth transferring use rails 11. At the retreated state of the traveling stand 12, the traveling stand 12 positions the bed 3 at a measurement preparation position, in that a position away from the dewar 4, where the patient 2 gets on and off the bed 3 as well as the posture of the patient 2 is corrected for the measurement, and at the advanced state the traveling stand 12 positions the bed 3 at a measurement position where the patient 2 is placed immediately under the dewar 4.

The elevation means 13 is disposed between the traveling stand 12 and the right and left direction moving means 14. The elevation means 13 elevates and deelevates the right and left direction moving means 14 (the bed 3) by a hydraulic expansion and contraction means constituted by a hydraulic cylinder and piston. Through manipulation of an elevation use hydraulic pump handle 17 pressurized oil is supplied in the hydraulic cylinder to elevate the right and left direction moving means 14, and when pushing a relief valve 18, the pressure oil in the hydraulic cylinder is discharged to deelevate the right and left direction moving means 14.

The right and left direction movement means 14 supports the bed 3 in such a manner to permit the bed 3 to move in right and left direction. When rotating a right and left transferring handle 16, the bed 3 is caused to move in right or left direction through a combination of a pinion and rack or a ball screw mechanism.

In order to place the patient 2 in a measurable condition in which the chest (the heart portion) of the patient 2 comes close to and immediately below the center of the bottom portion of the bewar 4, at first the traveling stand 12 is retreated along the back and forth direction transferring rails 11 to move the bed 3 to the measurement preparation position, thereafter, the patient 2 is laid on the bed 3 on the patient's back and the posture thereof is corrected. At this instance, the elevation means 14 deelevates the bed 3 to the lowest position or a predetermined height suitable for getting on and off the bed 3.

Thereafter, the traveling stand 12 is advanced along the back and forth transferring use rails 11 and moves the bed 3 to the measurement position under the dewar 4 to perform position matching of the heart center of the patient 2 with the bottom center of the dewar 4.

In order to match the heart center of the patient 2 with the bottom center of the dewar 4, it is necessary to perform the matching while observing a pin point marking of the heart of the patient 2 (usually the heart center position is estimated which is shifted by predetermined distances in X and Y axis directions from the position of a xiphoid process which is determined in advance through palpation, and this estimated position is determined as the pin point marking position). With this positioning method, because of the narrow space between the patient 2 and the dewar 4, the chest of the patient 2 is hidden behind the dewar 4 which causes insufficient confirmation of the positions of the dewar 4 and the pin point marking. For this reason, the setting is conventionally performed under insufficient matching, therefore, correlation between the sensor positions in the dewars 4 and the measurement portion is hardly taken which causes the position matching difficult. In particular, when many number (multi-channels) of magnetism sensors are arranged in the dewar 4, it was difficult to correlate the magnetism sensors for respective channels with the measurement portion.

The correlation between the magnetism sensors and the measurement portion is very important in data processing (position calibration) for the heart diagnosis. Further, it is possible to use the cardio magnetism measurement data in such a manner to superpose the same over an X ray image of the chest of the patient 2 to perform diagnosis such as to specify an abnormal portion of the heart, in such instance, the cardio magnetism measurement data (biomagnetic flux distribution) are superposed over the X ray image using the pin point marking as a guide, therefore, if the correlation between the magnetism sensors and the measurement portion can not be taken sufficiently as has been explained above, troubles are caused.

In order to countermeasure these problems, a biomagnetism measurement device having multi channel magnetism sensors, for example, as disclosed in JP-A-3-244433, is proposed in which a plurality of optical fibers serving as a collimator irradiating the measurement portion of the patient are prepared, these respective optical fibers are corresponded in one to one relation to respective pick-up coils (magnetism detection coils) incorporated in the dewar and the positioning between the measurement portion and the dewar is performed by using the lights (light spots) irradiated from the respective optical fibers as a guide. Further, in this conventional art the following position matching method between the dewar and the measurement portion is proposed, in that the collimator and the dewar are constituted separately and are disposed with a predetermined distance L, and when performing a measurement, at first a patient is laid on a moving stand (bed), then the moving stand is moved to a position opposing the collimator to set a position to be measured of the patient by the collimator, finally, the moving stand is moved (parallel displacement) by the distance L to a position opposing to the dewar.

However, even with the above explained method in which the lighting collimator and the dewar are disposed in separate positions with distance L, and the measurement portion and the position of light spots are matched in advance at a position remote from the dewar, thereafter, the patient is displaced by the distance L toward the dewar, when applying the multi-channel method, light sources and optical fibers each corresponding to the respective magnetism sensors have to be prepared, and further, when the body axis of the patient is inclined with respect to a coordinate axis of the dewar, it was impossible to detect the inclination with the light spots (when the measurement portion is specified under a body axis inclined condition, the position matching accuracy between the coordinate positions of the measurement position and these of the magnetism sensors is caused to vary and errors with respect to recognition of the respective positions of the measurement portion are resulted).

Further, a cardio magnetism measurement device as disclosed in JP-A-2-180244 proposes that in order to match a light beam (a light spot) from a light source with an index such as a marker attached to a patient, a top board of a bed on which the patient is laid is displaced, thereafter, the light source is retreated and at the very position where the light source was located a SQUID sensor is fixed.

Still further, JP(U)-A-57-13006 discloses still another conventional art in which a similar positioning is performed by making use of a like collimator.

However, among the conventional art in which the positioning use light spots are irradiated to the measurement portion of the patient in order to correlate between the magnetism sensors and the measurement portion, in the arrangement where the light collimator is provided at the bottom face of the dewar, when the dewar is caused to approach the patient, the light spots irradiated onto the patient can not be observed because the dewar blocks the visual field, therefore, the approaching distance of the dewar and the magnetism sensors is limited by itself.

After position matching between the heart center of the patient 2 and the bottom center of the dewar 4, through elevation of the bed 3 by manipulating the elevation use hydraulic pump handle 17, the patient 2 is, while observing visually, caused to approach to the bottom of the dewar 4.

Since the elevation amount of the bed 3 immediately below the dewar 4 varies depending on the body shape of the patient 2, the elevation amount has to be varied to a proper amount at every measurement, therefore, when the bed is excessively elevated, the patient 2 may be heavily caught between the dewar 4 and the bed 3 which causes problems with regard to manipulability and safety.

Further, when the elevation amount is short, an excessively large gap is set between the patient 2 and the bottom face of the dewar 4 which causes a problem of reducing measurement sensitivity.

Moreover, when the chest of the patient 2 approaches the dewar 4, opposing portions of the chest and the bottom face of the dewar 4 are hidden behind the dewar 4 which makes a visual observation of the degree of approaching of the bottom face of the dewar 4 difficult, resultantly, an operator has to perform the setting by the sixth sense which incurs a substantial burden on the operator.

DISCLOSURE OF THE INVENTION

The present invention is developed in view of the above problems, and an object of the present invention is to be provide a biomagnetism measurement device and a method of positioning a patient in the biomagnetism measurement device which permit an accurate and easy positioning between a dewar (magnetism sensors) and a measurement portion of the patient.

A present invention, which achieves the above object, is, in principle, constituted in the following manner.

According to a first aspect of the present invention, a biomagnetism measurement device comprising magnetism sensors including SQUIDs and a dewar which incorporates the magnetism sensors and is filled with a coolant so as to maintain the same in a super conducting state, is characterized in that the biomagnetism measurement device further comprises a light projecting means which projects cross shaped beam patterns used for positioning a measurement portion of a patient.

With the above construction, when performing a biomagnetism measurement, the positioning use cross shaped beam patterns are irradiate onto an inspection use patient laying apparatus (for example, an inspection use bed or chair), and a position matching is performed so that the crossing point of the beam patterns meets with a mark (pin point marking) at the center of the measurement portion of the patient (for example, an estimated position of the heart center). Further, thereafter, the center of the measurement portion is finally matched with the center of the dewar such as by performing position matching so that the center of the dewar meets with the crossing point of the cross shaped beam patterns on the patient laying apparatus and by relatively displaying the patient laying apparatus by a predetermined distance with respect to the dewar.

According to the present invention, the cross shaped beam patterns can be used as X and Y coordinate axes while assuming the crossing point as the origin, therefore, the crossing point of the cross shaped beam patterns is corresponded to the center of the measurement portion and the center of the dewar, and the positional relationship between the measurement portion and the multi channel magnetism sensors is correlated by making use of the X and Y coordinated axes. Different from an X ray CT and an MR imaging device, in a biomagnetism measurement device, the measured data do not contain any positional data of the measurement portion, therefore, the position matching between the measurement portion and the magnetism sensors is a very important technology. Further, when setting one of two axes of the cross shaped beam patterns, for example, Y axis in the body axis direction of the patient, and if the body axis is inclined with respect to the Y axis beam pattern, the inspection figure (inclination) of the patient can be corrected so that the body axis thereof meets with the Y axis beam pattern, thereby, a biomagnetism measurement can be performed with a correct posture of the patient (in other words, by correcting offsetting between the X axis and Y axis coordinate system of the dewar and that of the measurement portion of the patient).

A second aspect of the present invention, which is an application invention of the above first aspect invention, primarily comprises the magnetism sensors, the dewar and the light projecting means of the cross shaped beam patterns like the first aspect invention and in addition comprises marks which are used for setting X axis and Y axis coordinate system on the measurement portion of the patient.

These marks are attached in total at three points on the body of the patient, one representing the origin of the coordinate system and other two are respectively provided at any point on X axis and Y axis, and when a position matching between the patient (patient laying apparatus) and the dewar is performed so that these three points position on the cross shaped beam patterns, the correlation between the measurement portion of the patient and the dewar can be determined while eliminating a possible coordinate axes offsetting as much as possible.

A third aspect of the present invention which is also an application invention of the first aspect invention, is characterized in that the third aspect of the present invention primarily comprises a light projecting means which projects cross shaped beam patterns used for positioning the measurement portion of the patient on a measurement preparation position outside a position immediately below the dewar, wherein relative positions between a crossing point of the cross shaped beam patterns irradiated on the measurement preparation position outside the position immediately below the dewar and a position which is on an extension line passing the center of the dewar representing a measurement position immediately below the dewar are determined in advance, and further comprises a displacing means having a displacement amount control mechanism which effects a constant amount of transfer between the relative positions for at least one of the patient laying apparatus laying the patient thereon and the dewar.

According to the present invention, the cross shaped beam patterns are irradiated to the measurement preparation position which is never obstructed by the dewar and therein the patient laying apparatus is aligned and adjusted so that the measurement portion will meet with the crossing point of the cross shaped beam patterns, thereafter, it is possible to position the patient at the position immediately below the dewar by transferring the patient laying apparatus by a constant amount and at the same time the center of the measurement portion of the patient automatically meets with the center of the dewar.

A biomagnetism measurement device according to a fourth aspect of the present invention, which is also an application invention of the first aspect invention, primarily comprises the magnetism sensors and the dewar, is characterized in that the biomagnetism measurement device further comprises, a displacement means which freely transfers the patient laying apparatus laying the patient thereon for inspection between a measurement position immediately below the dewar and a measurement preparation position outside the position immediately below the dewar, and a light projecting means which projects cross shaped beam patterns used for positioning the measurement portion of the patient, and a first dewar mark used for performing position matching between X axis of the beam pattern and X axis of the dewar and a second dewar mark used for performing position matching between Y axis of the beam pattern and Y axis of the dewar are provided at the side face of the dewar, the light projecting means includes a first projector of which beam spreads in one direction and a second projector of which beam spread in a direction crossing the beam from the first projector, the first projector is disposed in such a manner that the beam spreading direction projected therefrom is in parallel with the free transferring direction of the patient laying apparatus and the beam covers the position outside the position immediately below the dewar and the first dewar center mark provided at the side face of the dewar, and the second projector is mounted and disposed on said displacement means in such a manner that the beam spreading direction projected therefrom is to be perpendicular to the free transferring direction of the displacement means.

According to the present invention, the cross shaped beam patterns are irradiated to the measurement preparation position which is not obstructed by the dewar by making use of the first and second projectors and therein a position matching is performed so that the measurement portion of the patient comes to the crossing point of the cross shaped beam patterns, thereafter, the patient laying apparatus is transferred in parallel with the beam spreading direction from the first projector until a position where the beam from the second projector which displaces together with the patient laying apparatus covers the second dewar mark provided on the side face of the dewar, thereby, a position matching between the crossing point of the cross shaped beam patterns (the center of the measurement portion) and the center of the dewar even at the measurement position immediately below the dewar is substantially facilitated.

A fifth aspect of the present invention relates to a positioning method making use of the above second and third aspects of the present invention and primarily comprises the following steps, in that when measuring magnetism of the measurement portion of the patient by making use of the dewar which maintains magnetism sensors including SQUIDs under a ultra low temperature, a patient laying apparatus laying a patient for inspection is located at a measurement preparation position outside a position immediately below the dewar, at the measurement preparation position outside the position immediately below the dewar the patient is laid on the patient laying apparatus under a condition of inspection figure, marks are attached at three points on the body of the patient so as to set X and Y coordinate axes on the measurement portion, further, cross shaped beam patterns are projected at the measurement preparation position outside the position immediately below the dewar, the position of the patient laying apparatus is adjusted so that the marks at the three points position on the cross shaped beam patterns, thereafter, the patient laying apparatus is transferred by a constant amount to a position immediately below the dewar, and the constant transferring amount is determined by the distance between the crossing point of the cross shaped beam patterns in the measurement preparation position and an extension line passing through the center of the dewar in the measurement position immediately below the dewar.

According to the present invention, only with the irradiation of the cross shaped beam patterns in the measurement preparation position outside the position immediately below the dewar and with the constant amount of transferring of the patient laying apparatus, the position matching between the measurement portion and the center of the dewar is realized, and, in addition, through introduction of the position matching method between the marks at the three points attached to the measurement portion of the patient and the cross shaped beam patterns, a positioning can be realized which further accurately determines the correlation of X and Y coordinate axes of the measurement portion and the dewar.

A sixth aspect of the present invention relates to a positioning method making use of the above second and fourth aspects of the present invention and primarily comprises the following steps, in that when measuring magnetism of the measurement portion of the patient by making use of the dewar which maintains magnetism sensors including SQUIDs under a ultra low temperature, a patient laying apparatus laying a patient for inspection is located via a displacement means at a measurement preparation position outside a position immediately below the dewar, at the measurement preparation position outside the position immediately below the dewar the patient is laid on the patient laying apparatus under a condition of inspection figure, marks are attached at three points on the measurement portion in advance so as to set X and Y coordinate axes, on the other hand, a first dewar mark used for performing position matching between X axis of the beam pattern and X axis of the dewar and a second dewar mark used for performing position matching between Y axis of the beam pattern and Y axis of the dewar are provided at the side face of the dewar, further two projectors are prepared which perform separate irradiation, among the two projectors the first projector is disposed in such a manner that the beam spreading direction projected therefrom is in parallel with the free transferring direction of the patient laying apparatus and the beam covers the position outside the position immediately below the dewar and the first dewar center mark provided at the side face of the dewar, and the second projector is mounted on the displacement means in such a manner that the beam spreading direction projected therefrom is to be perpendicular to the transferring direction of the patient laying apparatus, cross shaped beam patterns formed by making use of the first and second projector are projected at the position outside the position immediately below the dewar and the position of the patient laying apparatus is adjusted so that the marks at the three points attached to the patient locate on the cross shaped beam patterns, thereafter, the patient laying apparatus is transferred to the position immediately below the dewar by making use of the displacement means, and the transferring of the patient laying apparatus is effected until the beam projected from the second projector which displaces together with the patient laying apparatus meets with the second dewar mark.

According to the present invention, likely, only with the irradiation of the cross shaped beam patterns in the measurement preparation position outside the position immediately below the dewar and with the transferring of the patient laying apparatus (not limited to the constant amount of transferring), the position matching between the measurement portion and the center of the dewar is realized, and, in addition, through introduction of the position matching method between the marks at the three points attached to the measurement portion of the patient and the cross shaped beam patterns, a positioning can be realized which further accurately determines the correlation of X and Y coordinate axes of the measurement portion and the dewar.

Further, when the biomagnetism distribution data obtained according to the respective aspects of the present invention are superposed, for example, over a pseudo cardio pattern image or an actual heart image (X ray image), a positional correlation between the respective sensors and the respective portions of the heart can be determined, thereby, correlations between extraordinary output data of respective sensors in the dewar and portions of coronary abnormality and cardiac muscle abnormality of the heart are, for example, clarified which permits diagnosis on abnormal portions of the heart.

A biomagnetism measurement device according to a seventh aspect of the present invention comprises a dewar incorporating magnetism sensors and a patient laying means laying a patient thereon, is characterized in that the biomagnetism measurement device further comprises a gap detecting means which outputs a light beam so as to pass between a measurement preparation position outside a position immediately below the dewar and a measurement position immediately below the dewar while maintaining a slight distance with respect to the bottom face of the dewar and so as to detect interruption of the light beam due to approach of the patient to the bottom face of the dewar, wherein adjustment of a gap between the patient and the bottom face of the dewar is performed under a safe condition at the measurement preparation position and after adjusting the patient and the bottom face of the dewar at a predetermined gap, the patient is displaced to the measurement position, the details of the present invention will be explained later with reference to FIGS. 11 through 15.

Further, the seventh aspect of the present invention can be practice together with the first through sixth aspects of the present invention.

PREFERRED EMBODIMENTS FOR PRACTICING THE INVENTION

Figure 1:
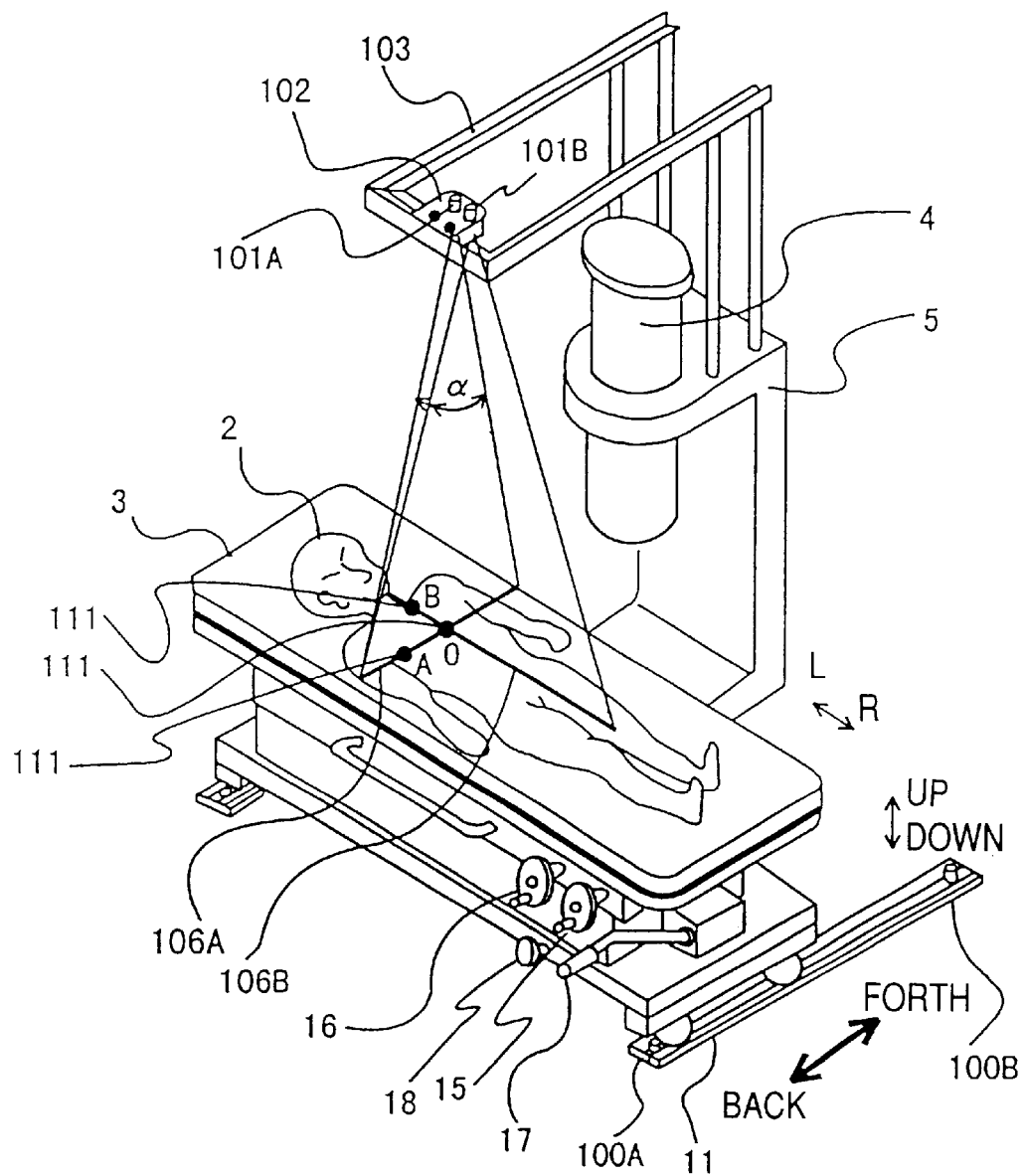
FIG. 1 is an outlook showing an entire structure of a biomagnetism measurement device representing a first embodiment according to the present invention.
Figure 2:
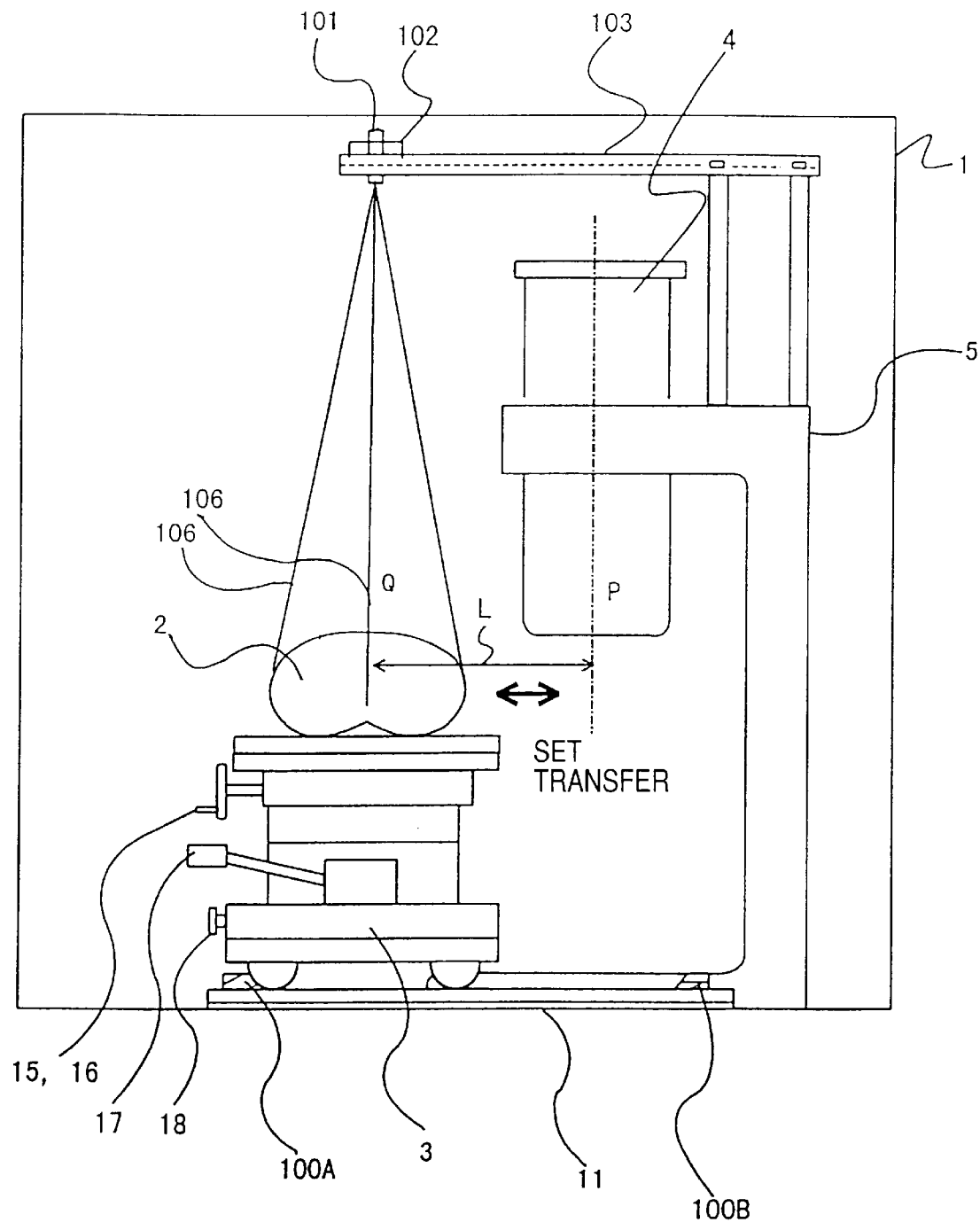
FIG. 2 is a constitution diagram viewed from the side face of the above biomagnetism measurement device.
Figure 3:
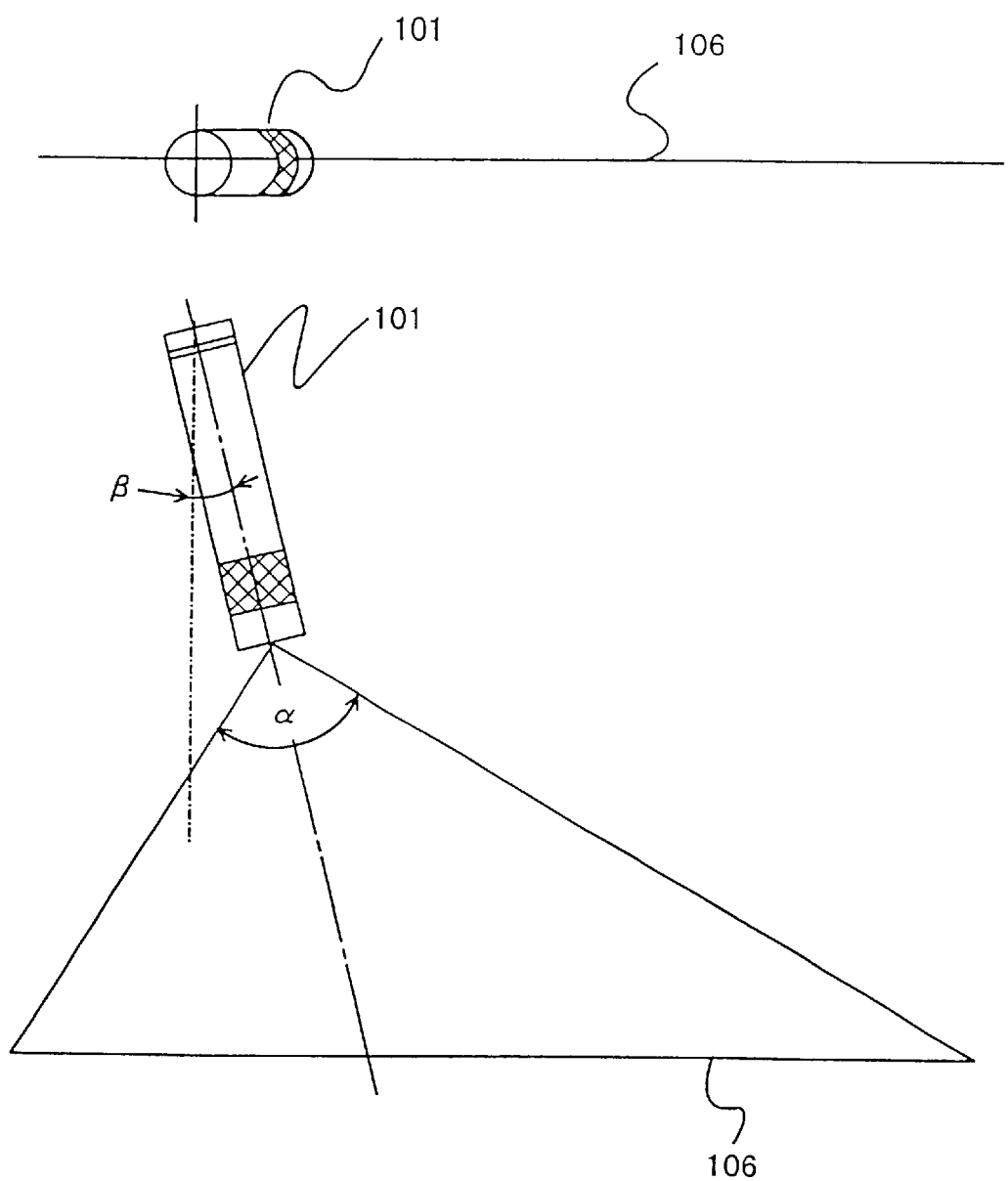
FIG. 3 is diagrams showing a tilt motion of a positioning use projector employed in the above embodiment and an output beam pattern thereof.
Figure 16:
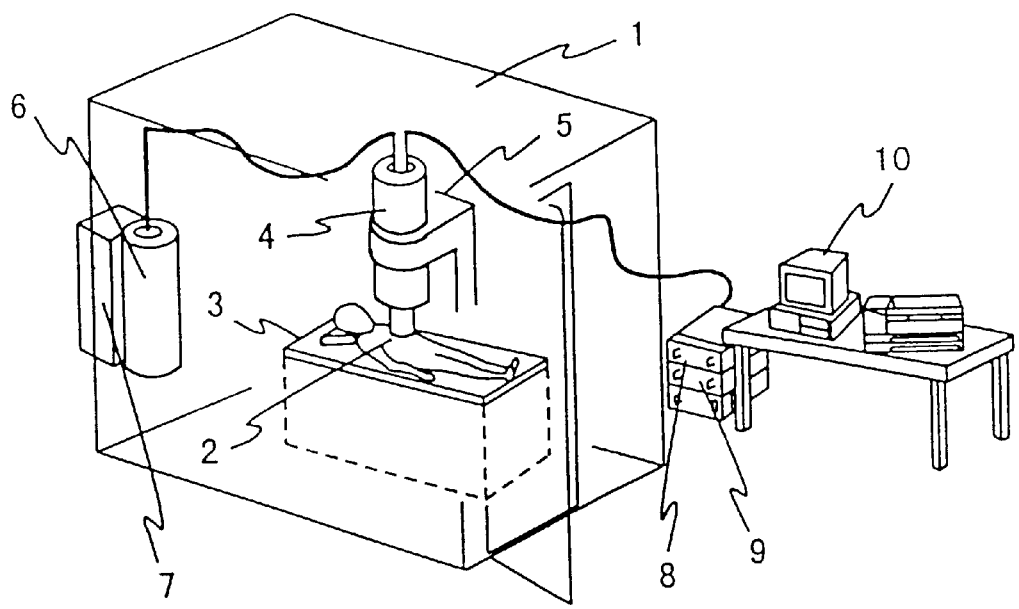
FIG. 16 is a construction diagram of a conventional cardio magnetism measurement system.
Figure 17:
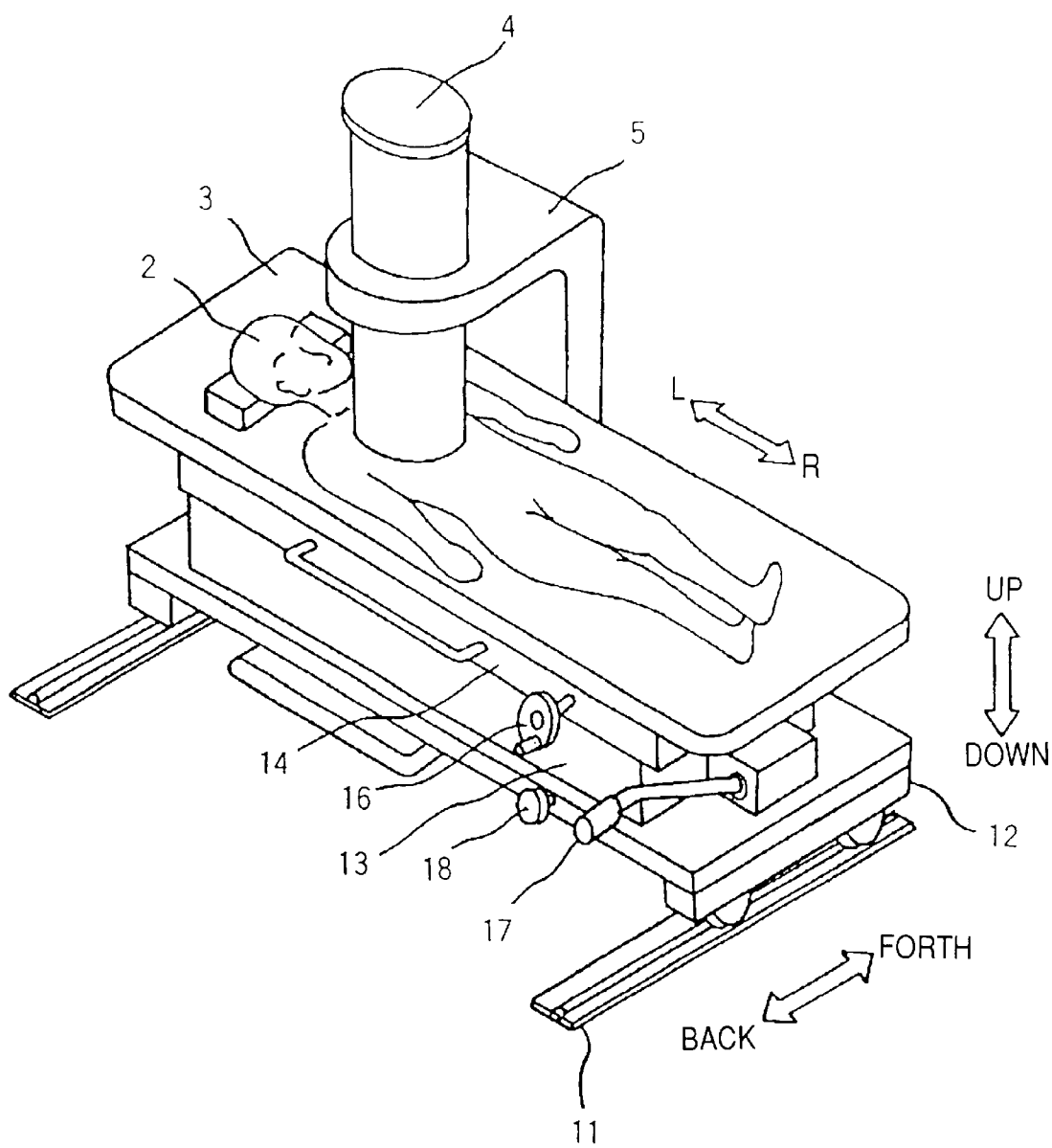
FIG. 17 is a perspective view of a conventional cardio magnetism measurement device.

Embodiments according to the present invention will be explained with reference to FIGS. 1 through 15. FIG. 1 is a perspective view showing an entire construction of a biomagnetism measurement device representing one embodiment according to the present invention and shows as an example a cardio magnetism measurement device. FIG. 2 is a side view used for explaining an operation for positioning a patient in the first embodiment, and FIG. 3 is an upper plane view and a front view of a light projecting unit used in the first embodiment. Further, the same reference numerals in FIGS. 1 through 3 as in already explained FIGS. 16 and 17 show the same or equivalent elements as those in FIGS. 16 and 17.

In the biomagnetism measurement device according to the present embodiment, primarily, a multi channel (a plurality of) magnetism sensors (not shown) are incorporated in a dewar 4, further, each of the magnetism sensors is constituted by a detection coil and a SQUID and is held in a ultra low temperature condition by liquid He introduced in the dewar 4 for maintain a super conducting condition of the magnetism sensors.

As shown in FIGS. 1 and 2, a bed 3 serving as a patient laying apparatus is set on bed transferring use rails 11 installed on a floor of a magnetically shielded room 1 so as to permit displacement in back and forth direction (in the width direction of the bed), and through this displacement the bed 3 can be transferred from a position P immediately below the dewar 4 to a predetermined position (a position retreated from the position immediately below the dewar 4) Q outside the position immediately below the dewar 4, and further stopping use rail stoppers (displacement amount limiting use stoppers 100) are disposed on the rails 11 at the positions P and Q so as to permit a constant amount of transferring between the positions P and Q.

On a gantry 5 holding the dewar 4 frames (supporting members) 103 used for supporting a projector holder are provided so as to protrude in horizontal direction from the position of the dewar 4, and at the protruding top portions of the frames 103 two light projectors 101 (101A, 101B) are disposed via holders 102. The two light projectors 101A and 101B are set so that cross shaped beam patterns (light marker) 106, which are used for positioning the measurement portion of a patient 2, are projected (irradiated) onto the predetermined position outside the position immediately below the dewar 4. The light projectors 101A and 101B are lamps or semiconductor lasers which output light beams having a frequency range of 300 nm~850 nm. The cross shaped beam patterns 106 are corresponded to X and Y coordinate axes of the dewar 4, and among the cross shaped beam patterns 106 light beam 106A spreading in X axis direction (in the back and forth constant amount transferring direction of the bed 3 or in bed width direction) is formed by the first light projector 101A, and light beam 106B spreading in Y axis direction (in bed longitudinal direction) perpendicular to the spreading direction of the light beam 106A is formed by the second light projector 101B. The crossing point of the light beams 106A and 106B is set at the aforesaid portion Q.

Through the setting of the crossing point of the cross shaped beam patterns as shown in FIG. 2 relative positions of the crossing point position Q of the cross shaped beam patterns projected onto the measurement preparation position outside the position immediately below the dewar 4 and position P immediately below the dewar 4 and an extension line passing through the center of the dewar 4 are set in advance. Further, with the rails 11 and the stoppers 100 a bed displacement arrangement having a displacement limiting mechanism is constituted which effects a constant amount of transferring (transferring amount of L) of the bed 3 between the relative positions P and Q.

The light projectors 101 (namely 101A and 101B) as shown in FIG. 3 are provided with a tilting (inclination) function which holds the light projector so as to permit free inclination adjustment by a desired angle β with respect to a vertical axis to the floor, and with this tilt mechanism a necessary and sufficient length (over the entire width and the entire body axis (the entire height) of the patient 2) of the beam linear pattern at the irradiation position can be obtained by varying the spreading angle α of the output light (beam) without changing the height position of the light projectors. Since the beam spreading angle α of the output light of the light projectors 101 is limited because of manufacturing limitation and if the irradiation direction of the light projector is simply directed in the vertical direction to the floor, the length of the beam patterns 106 are limited which sometime make impossible to irradiate the entire body width and the entire height of the patient 2, however, according to the present embodiment when the tilting function of any desired angle β is provided for the light projectors 101, the above inconvenience is resolved. The tilting function can be provided for one of the light projectors 101A and 101B.

Further, the light projecting unit forming the cross shaped beam patterns can be constituted by a single light projector which irradiates both beams spreading in X axis direction and ones spreading in Y axis direction, and in this instance, the spreading angle α of the output light is selected large from the beginning.

Other than constant amount transferring mechanism, the bed 3 is provided with a position adjusting mechanism of the bed 3 (a back and forth transferring handle 15) in X axis direction (in the back and forth transferring direction) of the cross shaped beam patterns, another position adjusting mechanism (right and left transferring handle 16) in Y axis direction (in the bed longitudinal direction) and a bed elevation manipulating unit (an elevation use hydraulic pump handle 17, an elevation and deelevation use relief valve 18).

Now, by making use of the device according to the present embodiment a positioning method is explained in which an estimated center position O of the measurement portion of the patient 2 matches with the center line of the dewar 4.

Figure 4:
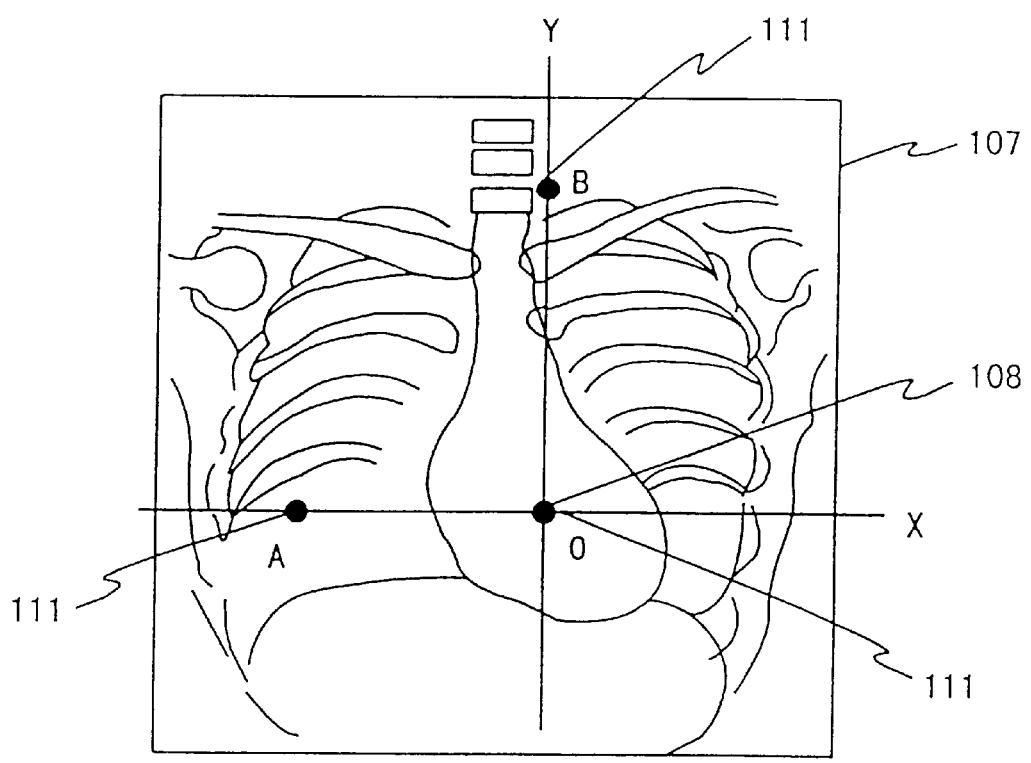
FIG. 4 is a view showing an X ray image taken while marking the chest of a patient with leads 111.
Figure 5:
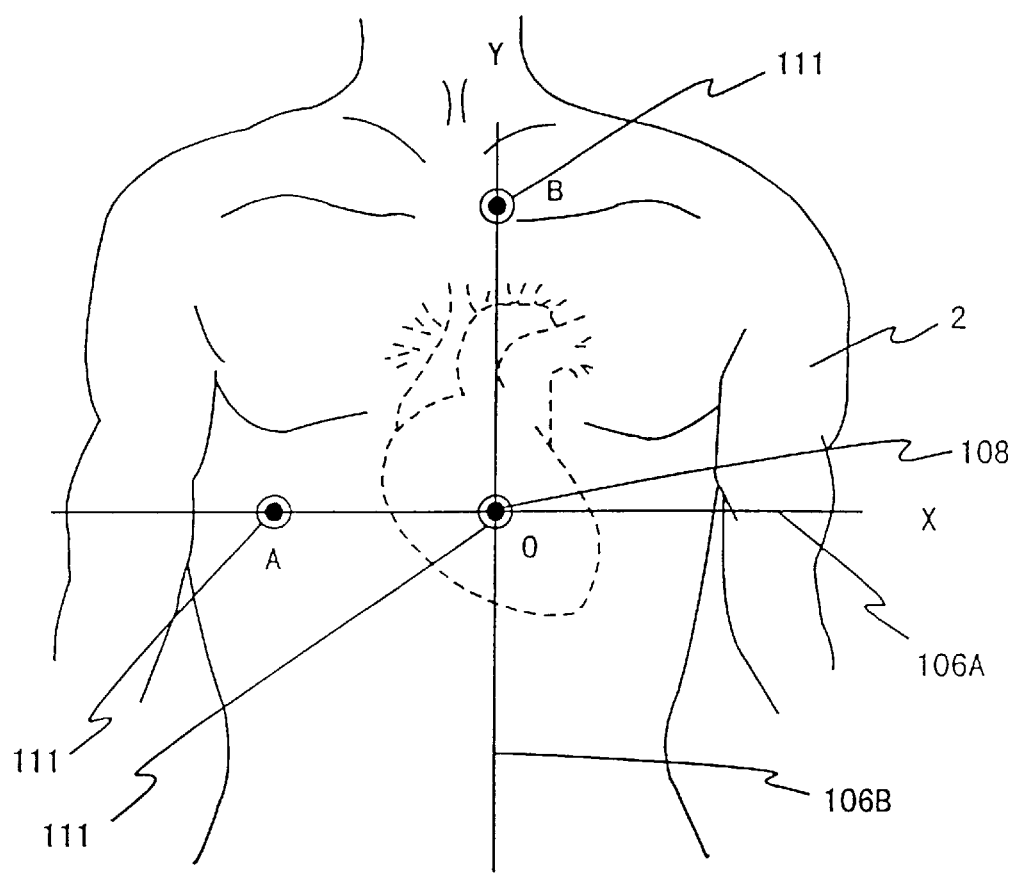
FIG. 5 is a view for explaining a condition, after marking the chest of the patient at three points by leads, and the markings are matched with cross shaped patterns.

As shown in FIGS. 1 and 5, three marks 111 which are used for setting X and Y coordinate axes on the measurement portion are attached beforehand on the body (chest) of the patient 2. Among the three marks 111, the mark at the point O serves for setting an estimated center position 108 of a heart constituting the measurement portion, the mark at the point A serves for setting X axis using the point O as the origin and the mark at the point B serves for setting Y axis using the point O as the origin, and these three marks are made of lead. The reason why the marks are made of lead is, when the cardio magnetism measurement data are used by superposing with an X ray image 107 of the patient, to facilitate the position matching thereof and to enhance the position matching accuracy. Namely, as illustrated in FIG. 4, when an X ray image of the chest is taken, the image of the three marks is also taken in the X ray chest image.

Further, the point O is usually determined in the following manner, in that through palpation the position of the xiphoid process of the body is searched and a position having predetermined distances in X and Y axis direction with reference to the searched xiphoid process position is determined as the estimated center of the heart.

When measuring magnetism of the measurement portion of the patient 2, the bed 3 is set at a position (a position where the bed 3 is stopped by the stoppers 100A) corresponding to the predetermined position Q representing the measurement preparation position outside the position immediately below the dewar 4, and the measurement preparation position outside the position immediately below the dewar 4 is determined as a position where the patient 2 gets on and off the bed 3 and where the patient 2 is laid on the bed 3 in an inspection posture.

Further, the light projectors 101A and 101B irradiate the cross shaped beam patterns 106 so that the crossing point of the beams 106A and 106B comes at the predetermined position Q outside the position immediately below the dewar 4.

Under this condition, the position of the bed 3 is adjusted via the back and forth transferring handle 15 and the right and left transferring handle 16 so that the marks 111 at the three points (O. A, B) on the patient 2 position on the cross shaped beam patterns 106 (so that the point O locates on the crossing point of the cross shaped beam patterns 106). During this position matching, the posture of the patient 2 is also corrected so that the body axis of the patient 2 does not inclined with respect to the cross shaped beam patterns.

Through this position matching, X and Y coordinate axes of the measurement portion and the cross shaped beam patterns are matched each other while eliminating any inclination of the body axis of the patient 2 with respect to the cross shaped beam patterns.

Subsequently, the bed 3 is transferred along the displacement rails 11 until being automatically stopped by the stoppers 100B. Thereby, the constant amount of transferring of the bed 3 by the displacement distance L is performed. As a result, the bed 3 comes immediately below the dewar 4 and the center position 108 of the heart of the patient 2 automatically matches with the bottom center of the dewar 4, and because the X and Y coordinate axes of both the dewar 4 and the patient match each other, the correlation between the measurement portion of the patient 2 and the magnetism sensors of respective channels in the dewar 4 is correctly determined.

Thereafter, the bed 3 is elevated through manipulation of the rising use hydraulic pump handle 17 so that the chest of the patient 2 approaches the bottom face of the dewar 4 and is stopped, then, through activation of the magnetism sensors a magnetism measurement of respective points (points facing the magnetism sensors of the respective channels) of the measurement portion is performed and the measured magnetism distribution data are then processed by a computer.

According to the present embodiment the following advantages can be obtained.

Through the use of a simple positioning measure as the cross shaped beam patterns and the constant amount transferring mechanism, the estimated center position 108 of the heart of the patient 2 can be position-matched with the center of the dewar 4 representing the magnetism sensors without being disturbed by the dewar 4, in addition inclination of the body axis of the patient 2 is also corrected, thus a correlation between the magnetism sensors of multi channels and the measurement portion can be easily and correctly taken.

Further, when the marks 111 made of lead are attached on the chest of the patient 2 at least at point O representing the estimated center position of the heart, at point A on X axis having a predetermined distance from point O and at point B on Y axis having a predetermined distance from point O, and the cross shaped beam patterns from the light projectors 101 are matched with these points, a positional correlation between an actual heart image taken by X ray and the respective magnetism sensors in the dewar 4 is clarified and an abnormal portion of the heart can be easily specified.

Figure 6:
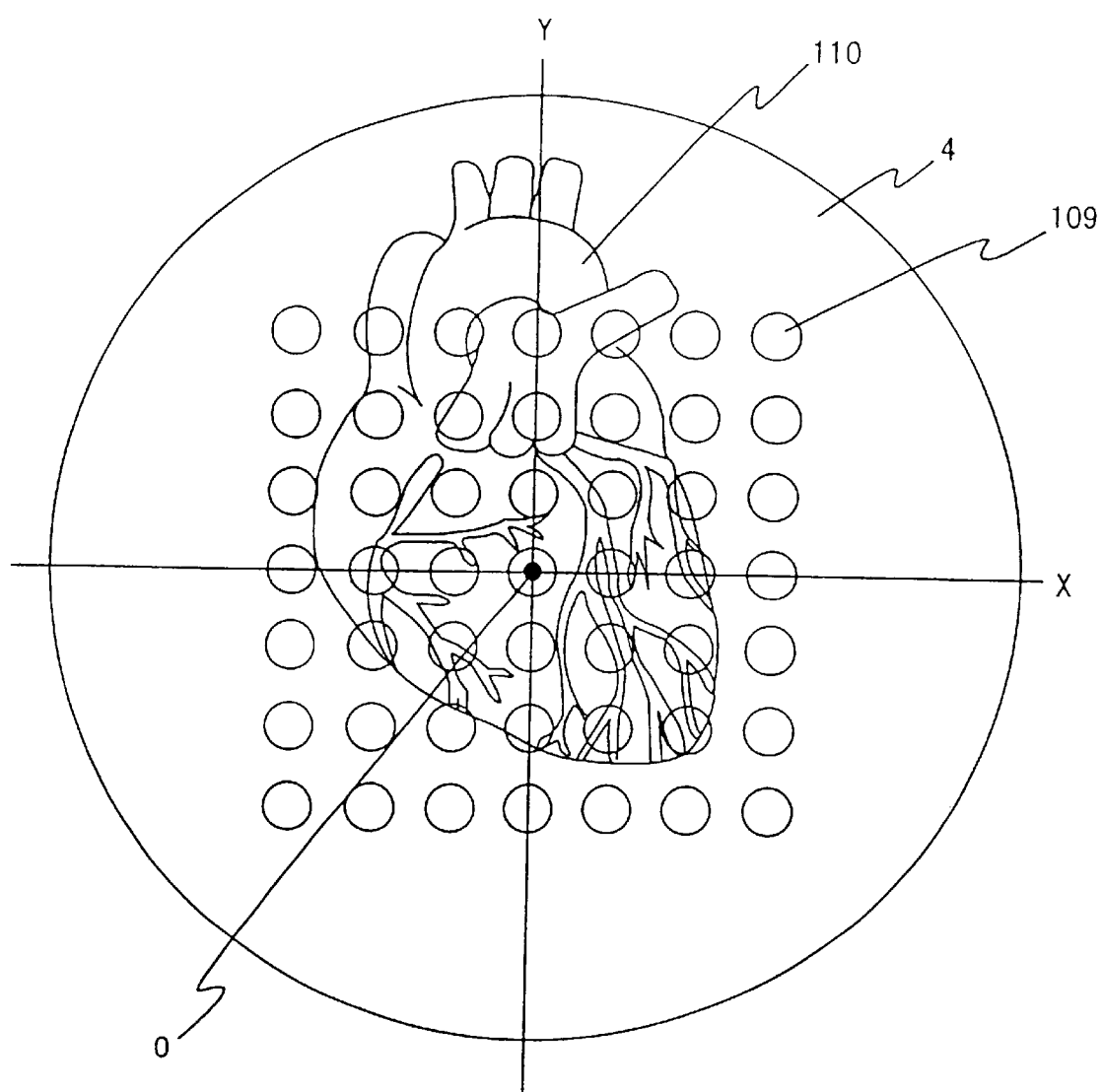
FIG. 6 is a processed image diagram which is formed by superposing a cardio magnetism data obtained according to the present invention over an X ray image taken or a pseudo cardio image.

Namely, FIG. 4 shows an X ray photograph 107 of the chest which was taken through X ray under a condition that the above lead marks 111 were attached on the patient 2, and when using this marking method, the X ray actual image of the heart and the positions of the marks 111 can be easily recognized and if the length O-A or O-B is determined beforehand, the actual size of the heart can be determined, further, when the photograph is graphically processed through a computer, an actual image of the heart (position, size and direction) can be drawn (digitalized) on X and Y axis coordinate system, still further when superposing the present photographic image, for example, over the cardio magnetism measurement data measured through the dewar 4 as illustrated in FIG. 6, it is possible to easily specify to which portion of the heart an abnormal portion judged from the signal data 109 outputted from the respective magnetism sensors corresponds (actually in data 109 represented by a circle O a vector having magnetism intensity and direction is recorded), thus diagnosis of heart diseases (coronary constriction, cardiac muscle abnormality, cardiac infarction) can be performed.

Further, in the above embodiment, the diagnosis method is exemplified in which the X ray photograph 107 of the chest of the patient 2 is superposed over the cardio magnetism measurement data, however, other than the above example, assuming that no X ray photograph of the chest is used, a normalized pseudo cardio image which is prepared in advance can be superposed over the cardio magnetism measurement data.

Further, cod-liver drops can be used for the marks 111. Since the cod-liver drops show a property to be caught as marks in a measurement image taken by an MR imaging device, it is advantageous when combining the biomagnetism measurement data with an MR image.

In the above embodiment, the marks 111 are used for three points, however, if the marks 111 are used at least for two points the cardio magnetism measurement data can be correctly superposed over the X ray photograph 107 of the chest. In such instance, it is sufficient, only if points A and B are marked by leads among the marks 111 at three points (O, A, B) in the above example. Even in the case when only two points are marked, the distances O-A and O-B can be utilized and further, since the mark 111 indicating the estimated center position (point O) of the heart does not appear in the X ray photograph 107 of the chest, a further effective diagnosis can be performed. The same is true with the use of the cod-liver drops. Of course, the marks can be placed for more than three points.

Further, it is preferable to select distance O-A and O-B more than 5 cm. In such instance, the position matching between the beam 106A and the line O-A and the beam 106B and the line O-B can be performed accurately and a possible overlapping of the marking points A and B on the very actual image of the heart such as in the X ray photograph is prevented.

Still further, in the above example, although the mark 111 is attached on the estimated center position 108 of the heart, the mark 111 can be attached on a body portion which is easily determined, for example, on the xiphoid process. Although the distances from the xiphoid process to the center of the heart in X and Y axis directions can vary depending on individuals, the distances can be represented by predetermined values (typical values) in view of statistical point. Accordingly, in such instance, the displacement distances by the constant amount transferring mechanism are offset by the typical value distances in X and Y axis directions or alternatively, the dewar 4 is disposed by offsetting by the typical value distance in X and Y axis directions, thereby the measurement portion (the center of the heart of the patient 2) can be matched with the center of the dewar 4. As a result, when performing measurement for a large number of patients in one time such as in a mass examination, the required position matching can be performed only through palpation of the xiphoid process, the possible positioning work by operators is greatly reduced and such examination can be performed in a short time.

Still further, the constant amount transferring between the bed 3 and the dewar 4 is relative one, therefore, the constant amount transferring can be carried out by displacing the dewar 4 or both the bed 3 and the dewar 4 can be displaced.

Now, another embodiment of the present invention will be explained with reference to FIGS. 7 through 11.

In the drawings, the same reference numerals as in the already explained first embodiment designate the same or equivalent elements as in the first embodiment.

Major differences of the present embodiment from the first embodiment are an arrangement of the light projectors 101A and 101B, a provision of first and second dewar marks 112A and 112B on the dewar 4 and elimination of the constant amount of transfer of the bed 3.

At first, the bed 3 is designed to be able to displace by a desired transferring amount in the back and forth direction (X axis direction) on the rails (wherein the rails 11 constitute the bed displacement arrangement for a desired bed transferring).

On the lower side face of the dewar 4, the first dewar mark 112A used for performing a position matching of X axis of the dewar 4 with the beam pattern 106A in X axis and the second dewar mark 112B used for performing a position matching of Y axis of the dewar 4 with the beam pattern 106B in Y axis are provided.

Figure 9:
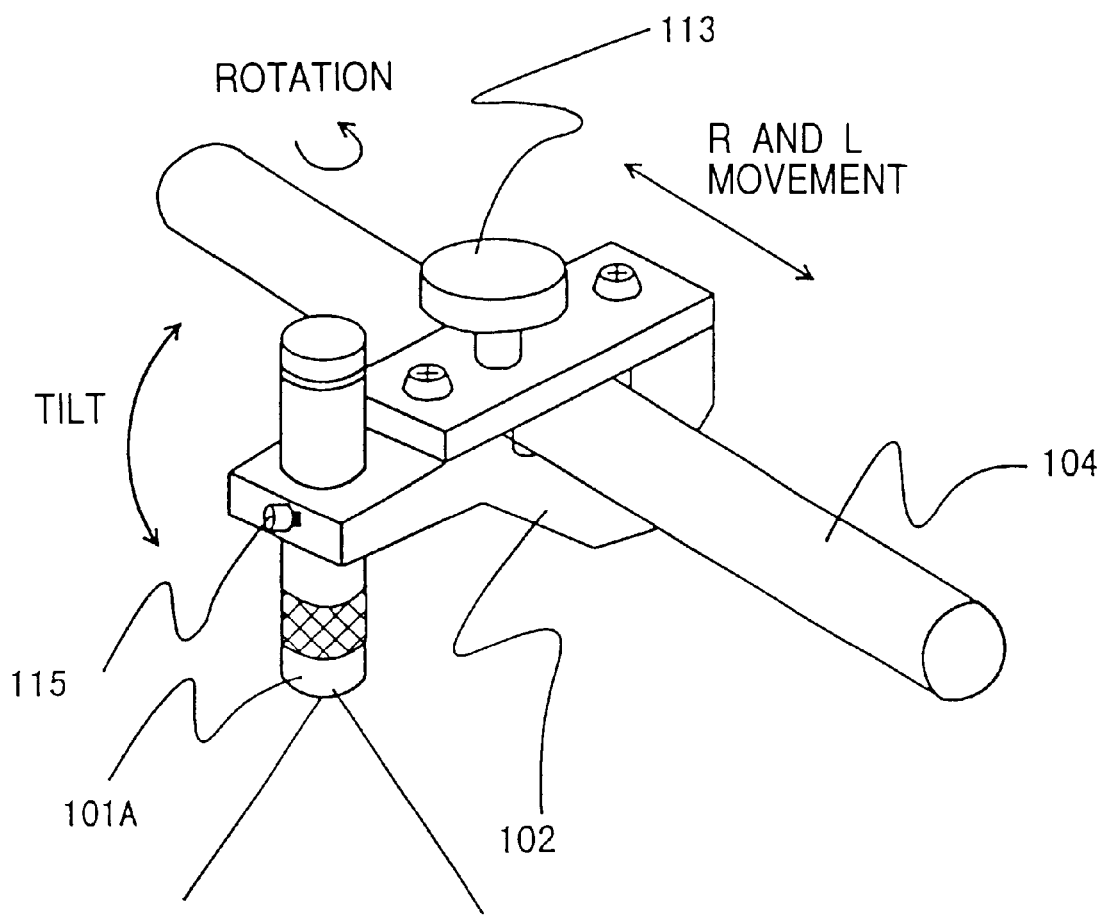
FIG. 9 is an explanatory view showing a position adjusting mechanism for a first projector used in the second embodiment.

The first light projector 101A is attached via a holder 102 at the top end of a pipe frame (a projector holder supporting member) 104 which is disposed above the dewar 4 and protrudes over the dewar 4 in horizontal direction. FIG. 9 shows the attachment details of the light projector 101A.

The holder 102 is secured onto the pipe frame 104 through fastening a securing use screw 113 as shown in FIG. 9, further, when the screw 113 is loosened, the holder 102 can rotate within a predetermined range in the horizontal direction such as by sliding on the pipe frame 104 in the frame axis direction (right and left direction) and by rotating around the pipe frame 104, and through these motions the light projecting position, the light projecting direction and the beam spreading angle of the light projector 101A are adjusted, thereafter the screw 113 is fastened and as a result the holder 102 as well as the light projector 101A are secured on the pipe frame 104. Further, through loosening a screw 105 the height position of the light projector 101A is finely adjusted.

Figure 7:
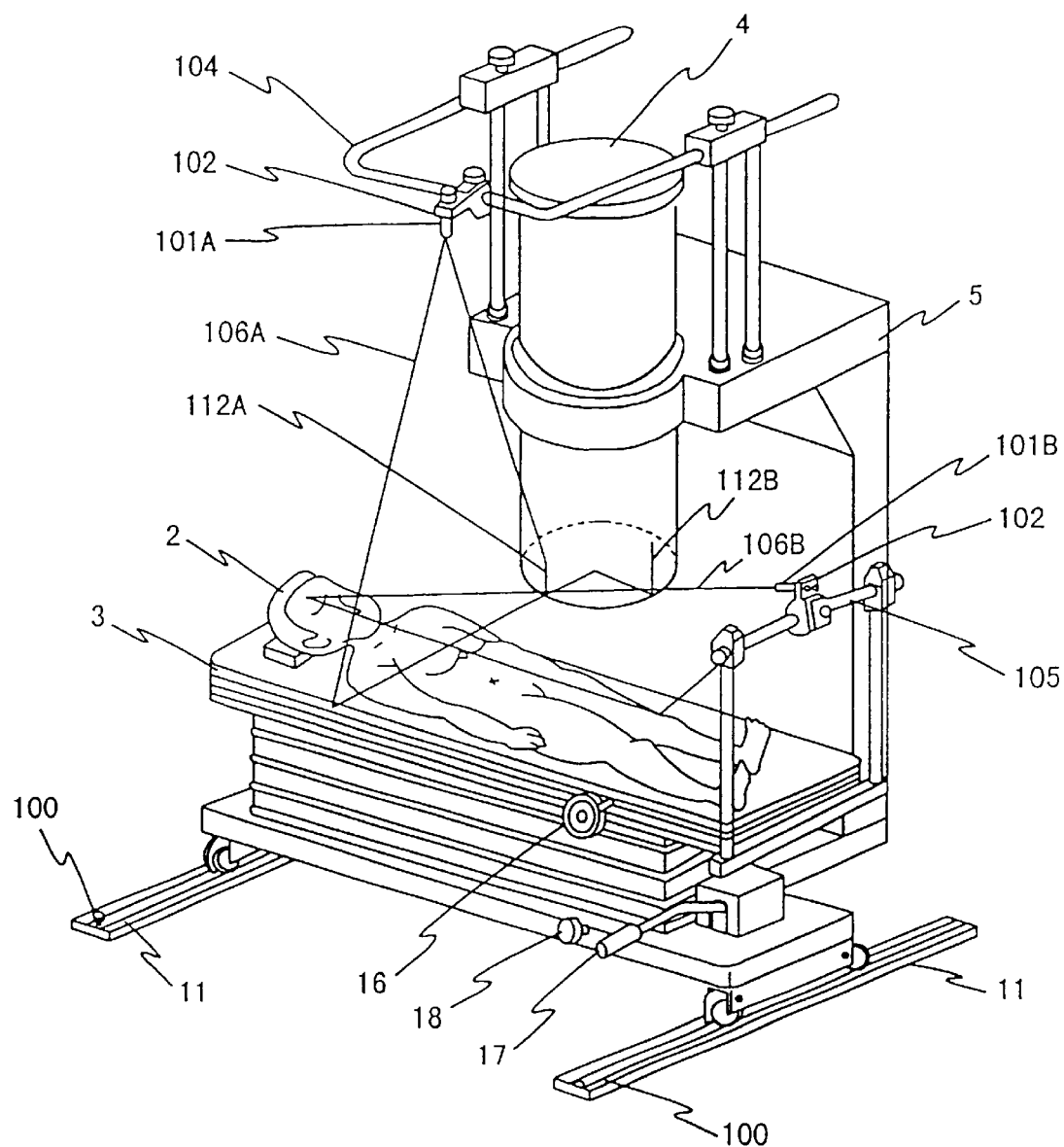
FIG. 7 is an outlook showing an entire structure of a biomagnetism measurement device representing a second embodiment according to the present invention.

Through the adjustment of the projecting position, the projecting direction and the beam spreading angle of the projector 101A, as shown in FIG. 7, the spreading direction of the projected beam 106A is set to be in parallel with the desired amount of bed transferring direction (X axis direction and the back and forth direction) by the bed displacement arrangement (rail) 11 as well as the beam 106A is set to cover the position outside the position immediately below the dewar 4 and the first dewar mark 112A provided on the side face. The beam 106A extends by the length of transversing the bed 3 in the width direction and the body of the patient 2.

Figure 10:
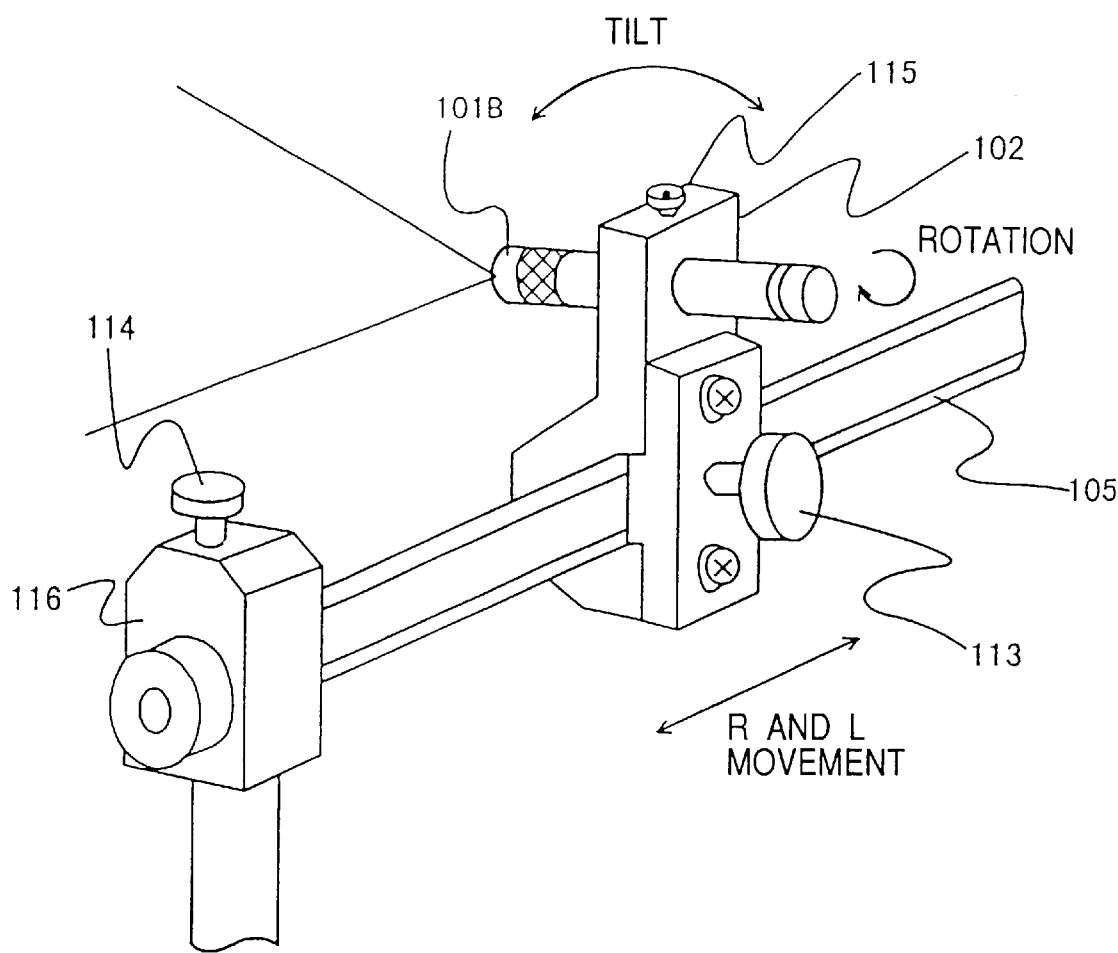
FIG. 10 is an explanatory view showing a position adjusting mechanism for a second projector used in the second embodiment.

The second projector 101B is mounted on the bed 3 so as to displace together with the bed 3 serving as the patient laying apparatus, and the spreading direction of the projected beam 106B is set in Y axis direction so as to be perpendicular (the bed longitudinal direction) to the desired amount of transferring direction of the bed 3. FIG. 10 shows the attachment details of the projector 101B.

The mounting position of the second projector 101B is selected among the two longitudinal ends of the bed 3 at one end of the bed 3 near the bed manipulation arrangement (the back and forth transferring handle 15, the right and left transferring handle 16 and the bed elevation manipulating unit 17). The second projector 101B is attached on a frame 105 provided at one end of the bed via another holder 102.

The holder 102 is secured on the frame 105 by fastening a securing use screw 113 as shown in FIG. 10, further, by loosening the screw 113, the holder 102 can slide on the frame 105 in the frame axis direction (right and left direction) as well as can rotate on the frame 105 in a predetermined range in the horizontal direction. Still further, the frame 105 serving as the holder support member is held by two parallel supporting posts 116 of the bed 3 so as to permit free rotation, and through rotation adjustment of the frame 105 the projector 101B is tilted by a desired angle, thereafter the position of the frame 105 is fixed with respect to the supporting posts 116 by fastening securing screw 114, thus the projection angle (tilt angle) of the projector 101B can be freely set. Further, the projection distance of the projector 101B can be finely adjusted by loosening a screw 115.

In the present embodiment, the position matching the measurement portion of the patient 2 and the dewar 4 is performed as follows.

At first, the bed 3 is set at the measurement preparation position outside the position immediately below the dewar 4 as shown in FIG. 7 by displacing the bed 3 on the rails 11, and herein the patient 2 is laid on the bed 3 in an inspection posture (laid on the patient's back). Then, an inspector adjusts the position of the projector 101B so that the beam pattern 106B spreading in the body axis (Y axis direction) of the patient 2 passes the marks at points B and O provided on the chest of the patient 2 (see FIG. 5), thereafter, further adjusts the bed 3 in right and left direction with the right and left transferring handle 16 so that the beam pattern (X axis direction beam pattern) irradiated from the projector 101A passes through the marked points A and O on the patient 2 (see FIG. 5).

Namely, the cross shaped beam patterns 106 formed by making use of the projectors 101A and 101B are projected onto the position outside the position immediately below the dewar 4, and the position of the bed 3 is adjusted relatively with respect to the patterns 106A and 106B so that the marks (which corresponds to the marks 111 in FIGS. 1 and 5) at three points attached to the patient 2 locate on the cross shaped beam patterns 106.

Figure 8:
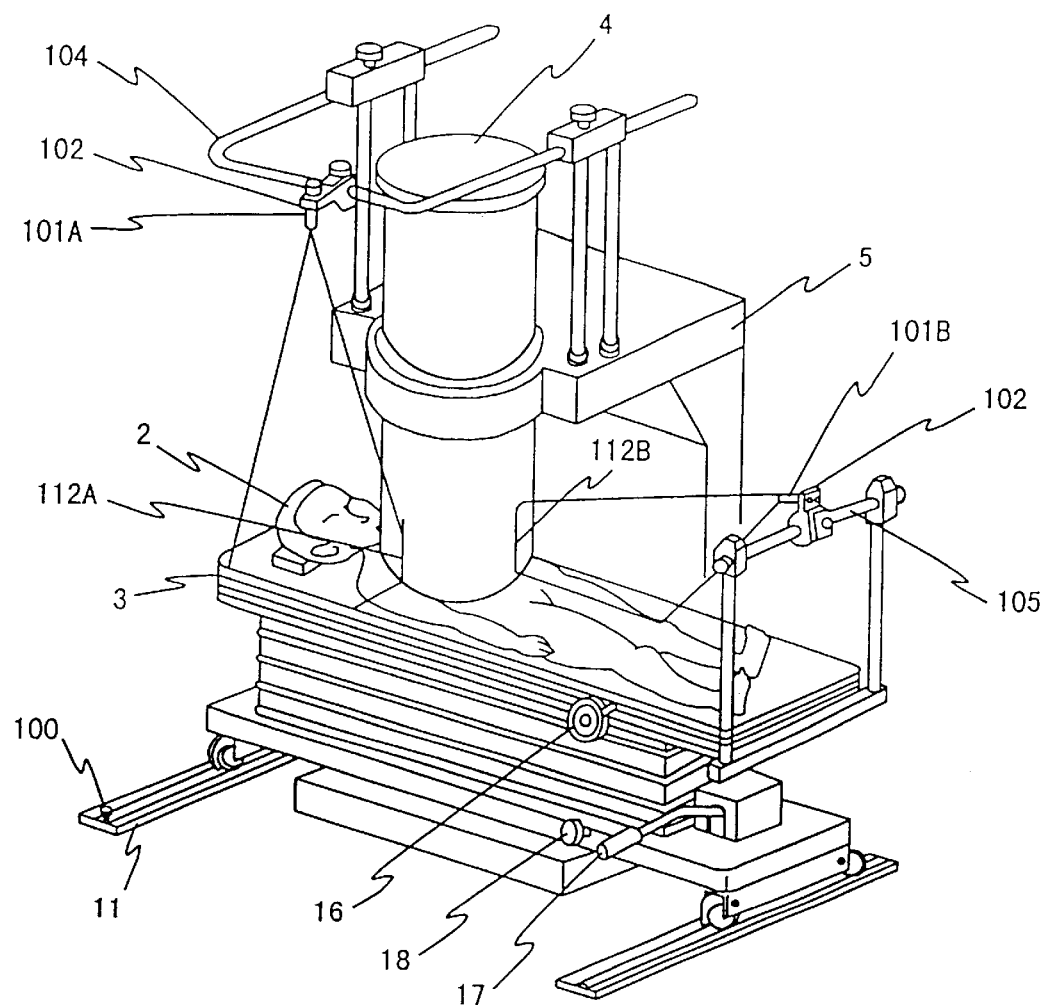
FIG. 8 is an outlook showing a state when a position matching between a patient and a dewar has been completed in the second embodiment.

Subsequently, the bed 3 is moved on the rails 11 serving as the bed displacement arrangement and is transferred immediately below the dewar 4 so that the beam 106B projected from the second projector 101B matches with the second dewar mark 112B provided on the side face of the dewar 4 as shown in FIG. 8.

With the above operation, even in the measurement position immediately below the dewar 4 the position matching between the crossing center (the center of the measurement portion) of the cross shaped beam patterns 106A and 106B and the center of the dewar 4 is performed automatically and easily. Further, only with the irradiation of the cross shaped beam patterns onto the patient 2 outside the position immediately below the dewar 4 and the bed transfer (not necessarily the constant amount of transfer), the position matching between the measurement portion and the center of the dewar 4 is realized, and through the use of the method in which the marks at the three points attached on the measurement portion of the patient 2 matches with the cross shaped beam patterns, a positioning which further correctly determines the correlation between X and Y axis coordinates of the measurement portion and the dewar 4 can be achieved.

Accordingly, like the first embodiment, the estimated center position 108 of the heart of the patient 2 can be position-matched with the center of the dewar 4 including the magnetism sensors without being obstructed by the dewar 4, as well as the correlation between the magnetism sensors for multi channels and the measurement portion can be taken correctly and easily.

Further, after the position matching between the center of the dewar 4 and the center of the measurement portion of the patient 2, the patient 2 is approached to the bottom face of the dewar 4 through elevation of the bed 3, thereafter, the biomagnetism measurement is performed like the first embodiment.

Still further, in the above example, although the point O (the measurement portion) is used as the estimated center position 108 of the heart, the mark 111 can be attached on a body portion which is easily determined, for example, on the xiphoid process. Although the distances from the xiphoid process to the center of the heart in X and Y axis directions can vary depending on individuals, the distances can be represented by predetermined values (typical values) in view of statistical point. Accordingly, in such instance, if the dewar marks 112 on the side face of the dewar 4 are positioned by offsetting by the typical value distances in X and Y axis directions toward the xiphoid process from the center of the dewar 4, thereby, the measurement portion (the center of the heart of the patient 2) can be matched with the center of the dewar 4. Of course, the offset distances (the distances from the center of the dewar 4) of the dewar marks 112 on the side face of the dewar 4 are already known, the correlation between the beam patterns 106 and the positions of the magnetism sensors for the respective channels in the dewar 4 is also taken, therefore, as a matter of course the positional correlation between the measurement portion of the patient 2 and the magnetism sensors can correctly be taken. As a result, when performing measurement for a large number of patients in one time such as in a mass examination, the required position matching can be performed only through palpation of the xiphoid process, the possible positioning work by operators is greatly reduced and such examination can be performed in a short time.

Still further, in the above embodiment the bed displacement direction is in parallel with the beam spreading direction, however, even if not in parallel, the position matching between the measurement portion and the center of the dewar can, of course, be performed.

Still further, in the above embodiment the two beams are in perpendicular relation, however, even if not in perpendicular relation, the position matching between the measurement portion and the center of the dewar can, of course, be performed.

Now, still another embodiment according to the present invention will be explained with reference to FIGS. 11 through 14.

Figure 11:
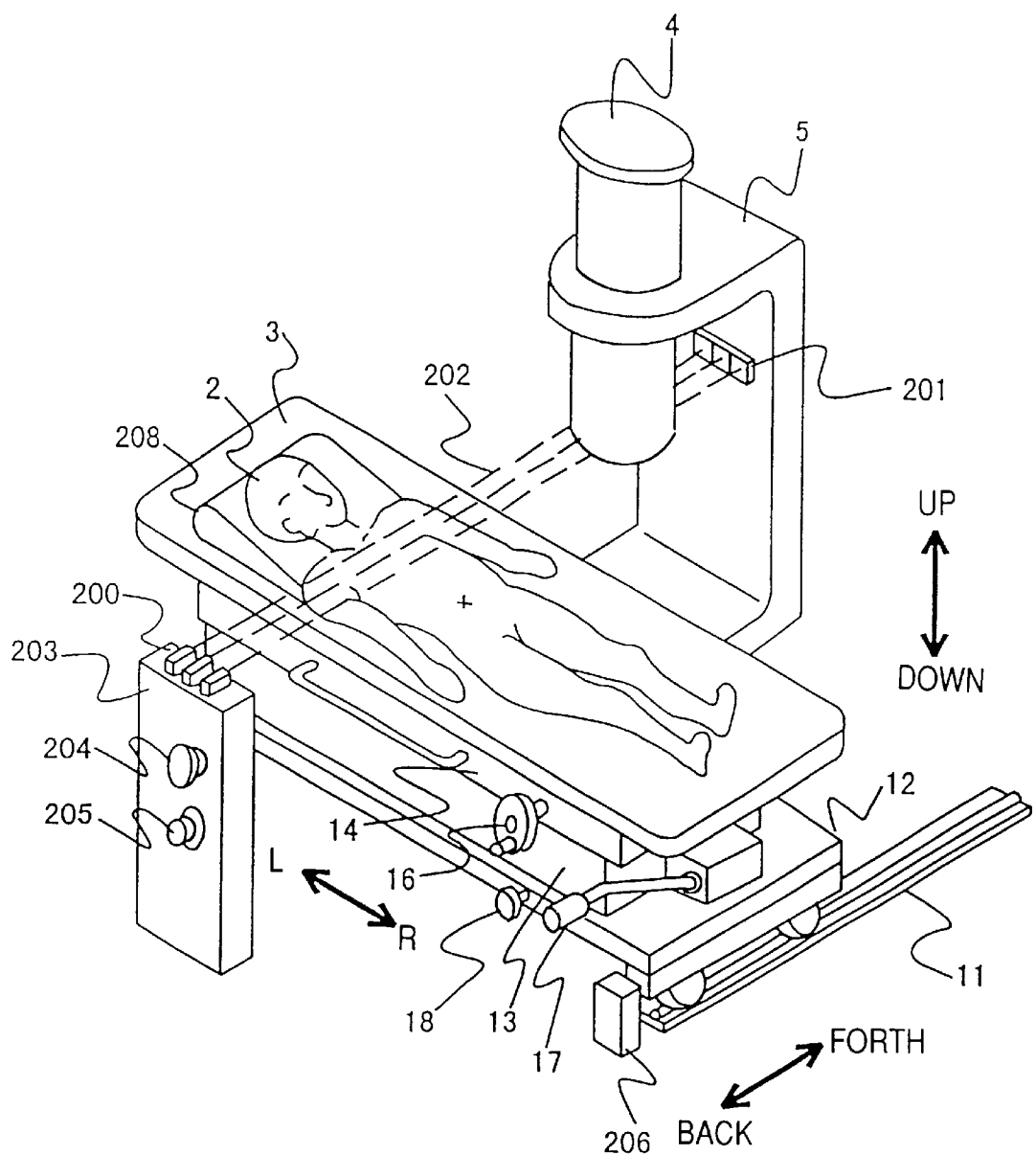
FIG. 11 is a perspective view of a cardio magnetism measurement device representing a third embodiment according to the present invention.
Figure 12:
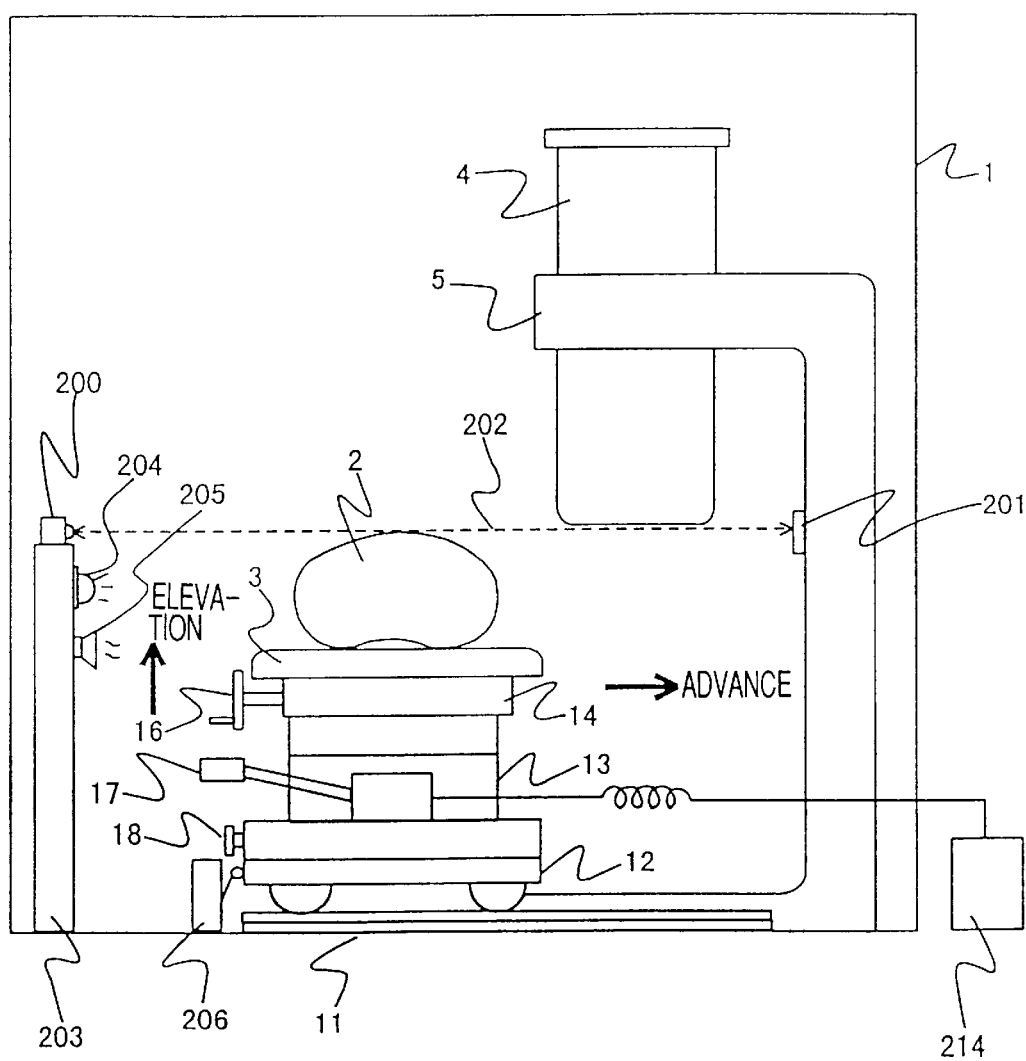
FIG. 12 is a side view of the cardio magnetism measurement device of the third embodiment.
Figure 13:
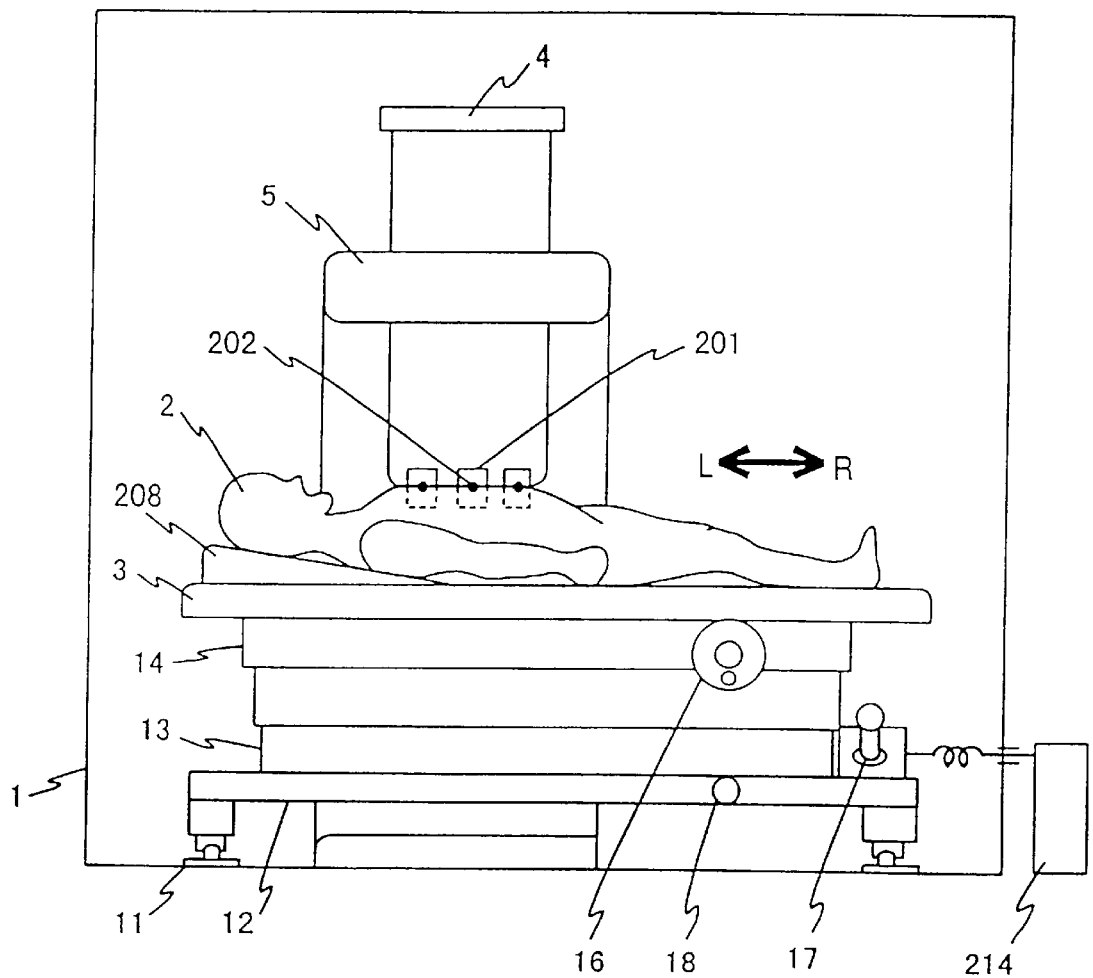
FIG. 13 is a front view of the cardio magnetism measurement device of the third embodiment.
Figure 14:
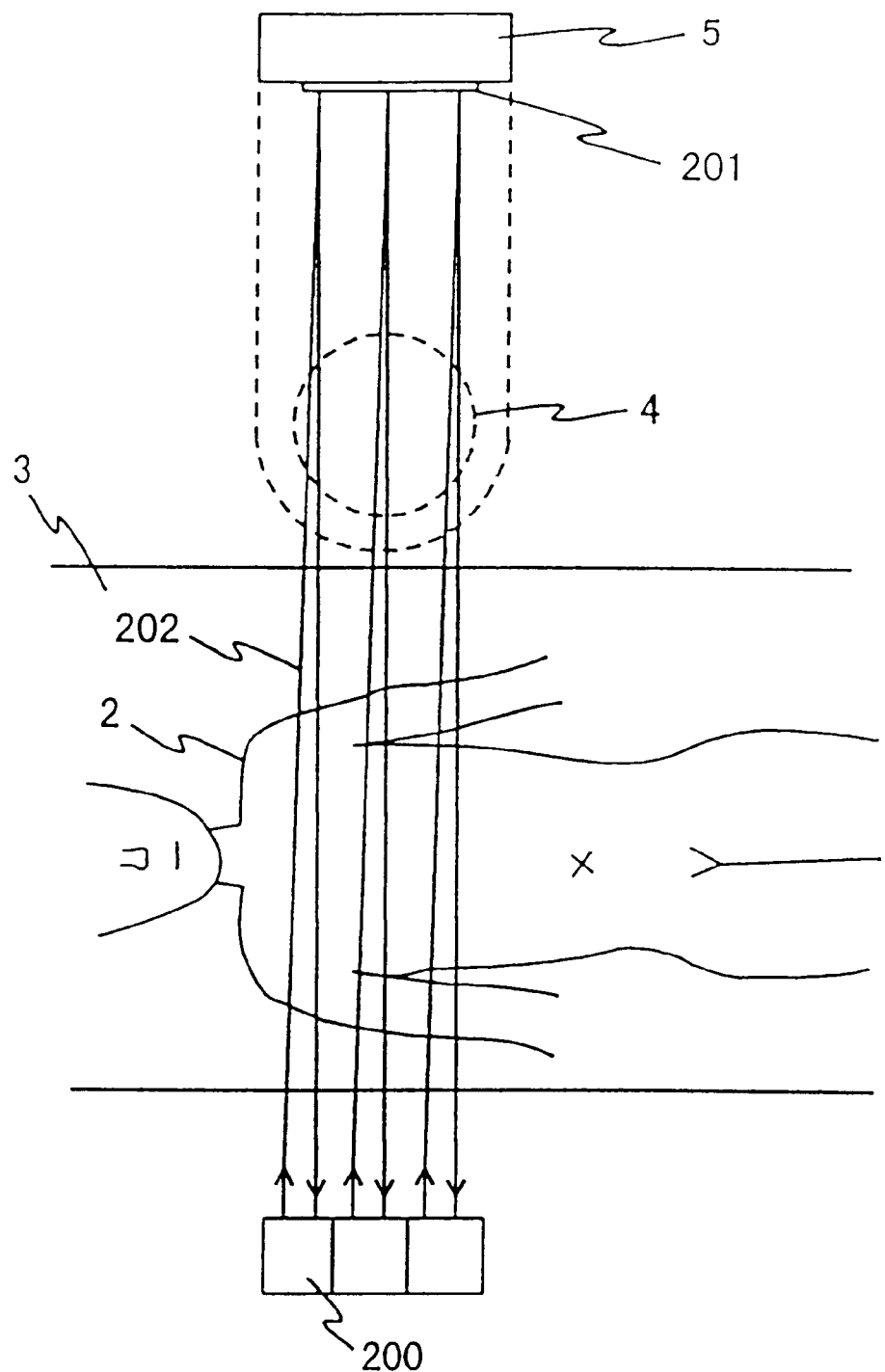
FIG. 14 is a plane view of a part of the cardio magnetism measurement device of the third embodiment.

FIG. 11 is a perspective view of a cardio magnetism measurement device according to the present invention, FIG. 12 is a side view thereof, FIG. 13 is a front view thereof and FIG. 14 is a plane view a part thereof. All of the drawings show a state where the bed 3 for laying the patient 2 is positioned at the measurement preparation position which is remote from the measurement position immediately below the dewar 4 and in which the patient 2 gets on and off the bed 3 and the height of the bed 3 is adjusted.

A gap detection unit which detects a gap between the chest of the patient 2 and the bottom face of the dewar 4 is constituted by a reflection type photo-electric switch 200 and a reflection mirror 201. The reflection type photoelectric switch 200 incorporates a light emitting unit outputting light beams 202 and a light receiving unit receiving reflected returning light beams which are arranged in lateral direction. The reflection type photoelectric switch 200 and the reflection mirror 201 are mounted on a detection stand 203 disposed outside the measurement preparation position and on the gantry 5. The light beam 202 goes and comes passing through the measurement preparation position and the measurement position substantially in parallel with the lateral moving locus in the advance and retreating direction of bed 3 (in the direction of the back and forth rails 11) while maintaining a slight distance from the bottom face of the dewar 4.

The reflection type photoelectric switch 200 and the reflection mirror 201 are arranged in such a manner as illustrated in FIG. 14 that the light beams 202 outputted from the light emitting unit of the reflection type photoelectric switch 200 are caused to pass the measurement preparation position and the measurement position, and when reflecting the same by the reflection mirror 201, the reflected light beams are directed to the light receiving unit which is positioned at the same height as the emitting unit but is offset in lateral direction. Namely, the go and come route of light beams are differentiated to thereby increase a gap detection range and to enhance a detection accuracy. Further, by arranging a plurality of pairs of the reflection type photoelectric switch 200 and the reflection mirror 201 at a same height, the gap detection accuracy is further enhanced. Of course, it is possible to constitute the gap detection arrangement by making use of a transmission type photoelectric switch and by disposing the light receiving unit at the position of the reflection mirror 201. Further, the present embodiment can be practiced even if the light beams 202 are not set in parallel with the lateral moving locus in the advance and retreating direction of the bed 3.

It is preferable that the light beams 202 pass below the bottom face of the dewar 4 in the distance 1~50 mm. If the distance is set less than 1 mm, the chest of the patient 2 can touch the bottom face of the dewar 4 during respiration, and magnetism noises can be measured by the magnetism sensors which makes a correct measurement of biomagnetism difficult. Further, if the distance between the chest face of the patient 2 and the bottom face of the dewar 4 is more than 50 mm, namely the distance between the measurement portion and the magnetic sensors is greatly separated, which makes a correct measurement of weak biomagnetism difficult.

An indication lamp 204 and a buzzer 205 constituting an alarm unit is mounted on the detection stand 203.

A preparation position detection unit which detects that the bed 3 laying the patient 2 is positioned at the measurement preparation position uses a micro switch 206 which is disposed so as to respond to the traveling stand 12 positioned at the measurement preparation position.

Figure 15:
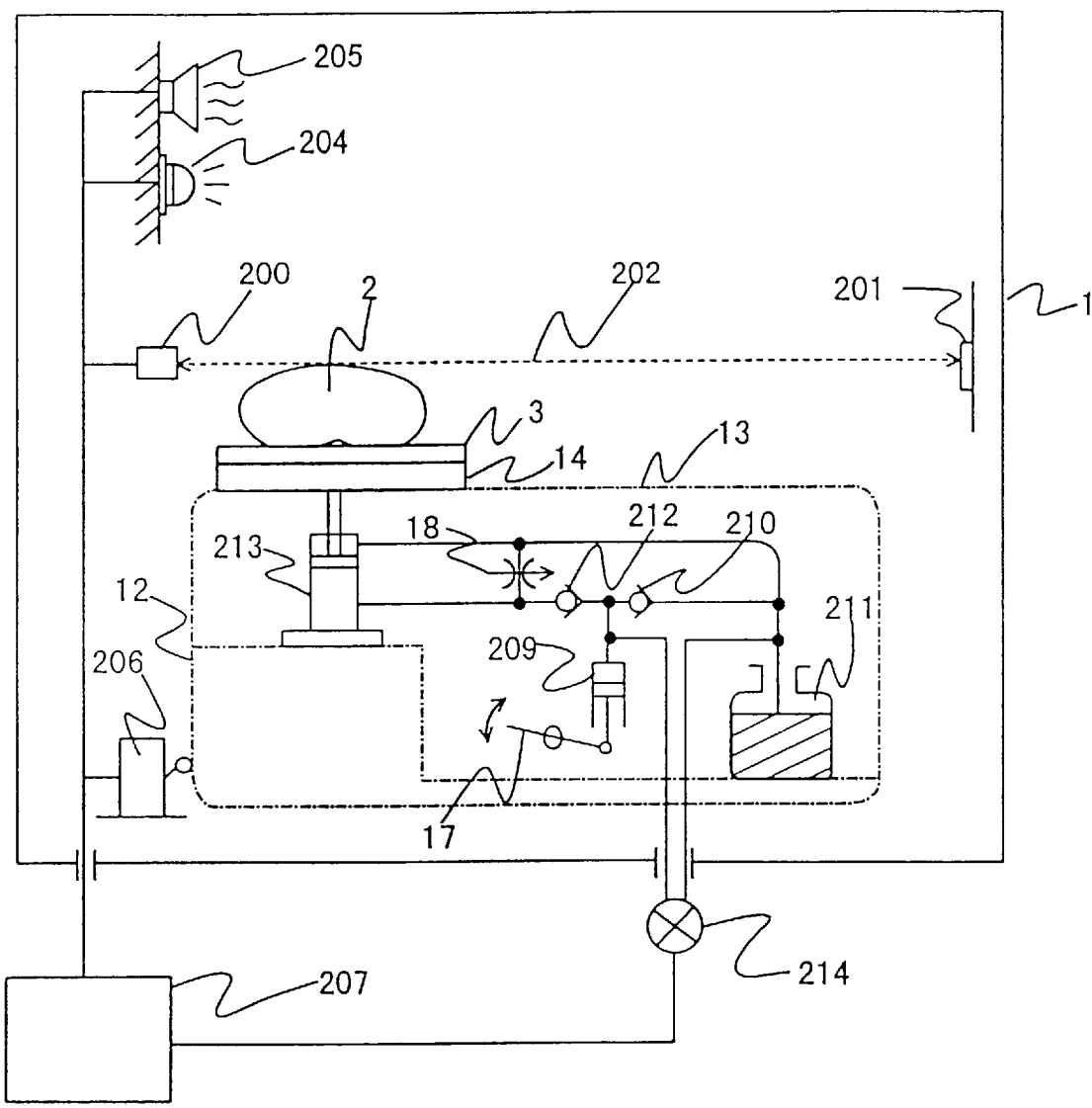
FIG. 15 is an electric and hydraulic system diagram in the cardio magnetism measurement device of the third embodiment.

FIG. 15 is an electric and hydraulic system diagram in the cardio magnetism measurement device according to the present invention.

A hydraulic pump 209, which is operated through manipulation of the rising use hydraulic pump handle 17, sucks oil from an oil tank 211 via a check valve 210 and supplies the oil to a hydraulic cylinder 213 via a check valve 212 to elevate the right and left lateral displacement unit 14. The relief valve 18 causes to discharge the oil contained in the hydraulic cylinder 213 into the oil tank 211 to deelevate the right and left lateral displacement unit 14. A solenoid valve 214 which invalidates the oil supplying function of the hydraulic pump 209 by short circuiting the check valve 209 is disposed outside the magnetically shielded room 1, because a valve body made of a magnetic material in the solenoid valve 214 causes an adverse effect to the measurement.

A control unit 207 is disposed outside the magnetically shielded room 1, receives as its inputs the gap detection signals in connection with the patient 2 from the photoelectric switch 200 and the measurement preparation position detection signals in connection with the traveling stand 12 from the microswitch 206 and performs controls for the solenoid valve 214, the indication lamp 204 and the buzzer 205.

For the cardio magnetism measurement with such cardio magnetism measurement device, at first the traveling stand 12 is displaced and retreated back to the measurement preparation position, and the hydraulic cylinder 213 is discharged by releasing the relief valve 18 to lower the bed 3 to the lowest position or an optimum position for getting on and off of the patient 2. Then, the patient 2 is laid on the bed 3 on the patient's back and the posture of the patient 2 is corrected in a measurement posture by using a wedge shaped pillow or by inclining the top board of the bed 3, and through the lateral displacement of the bed 3 in right and left direction by manipulating the right and left transferring handle 16 in the right and left lateral displacement unit 14, the bed 3 is positioned in such a manner that the chest is positioned on the advance and retreating locus passing through the dewar 4 so that when the patient 2 is advanced the chest thereof faces the dewar 4. When the traveling stand 12 is retreated to the measurement preparation position, since the microswitch 206 responds thereto and generates the measurement preparation position detecting signals, the control unit 207 puts the solenoid valve 214 in an interrupted condition so as to permit elevation of the bed 3 through manipulation of the hydraulic pump handle 17.

When the bed 3 is in a lower position and the patient 2 does not interrupt the light beams 202, the photoelectric switch 200 outputs patient non-detecting signals, therefore, the control unit 207 controls to turn on the indication lamp 204 and to silence the buzzer 205.

Under the above condition, when the hydraulic pump handle 17 is manipulated, the hydraulic cylinder is charged to elevate the bed 3. Thereafter, when the upper most portion of the chest of the patient 2 is elevated up to the level of the light beams 202 passing between the photoelectric switch 200 and the reflection mirror 201 and interrupts the light beams 202, the photoelectric switch 200 responds thereto and outputs patient detecting signals. The control unit 207 responds to the patient detecting signals and controls to turn off the indication lamp 204 and to blow the buzzer 205 for a predetermined period for alarming, and further to release the flow passage of the solenoid valve 214 disposed outside the magnetically shielded room 1. Thereby, if the hydraulic pump 209 is driven by manipulating the hydraulic pump handle 17, the pressure oil is released into the oil tank 211, the hydraulic cylinder 213 can not be elevated any more and the elevation of the bed 3 is stopped. At this moment, the chest of the patient 2 positions at a level slightly below (for example, about 5 mm) the level of the dewar 4.

Thereafter, under the above condition the traveling stand 12 is pushed, advanced along the back and forth transferring rails 11 and displaced to the measurement position. At this measurement position, the chest of the patient 2 positions immediately below the dewar 4 and close to the center thereof which forms an optimum condition for the measurement.

After completing the measurement, the traveling stand 12 is retreated while maintaining the height as it is, and the bed 3 is pulled out from the measurement position immediately below the dewar 4 and is displaced to the measurement preparation position where the relief valve 18 is opened to lower the bed 3, or after opening the relief valve 18 and lowering the bed 3, the traveling stand 12 is retreated to the measurement preparation position so as to permit the patient 2 to get off the bed 3 safely.

As has been explained above, since the light beams 202 are passed through the measurement preparation position remote from the dewar 4 and the measurement position at a level slightly separated from the bottom face of the dewar 4 and in parallel with the advance and retreating locus, the patient 2 gets on and off the bed 3 at the measurement preparation position, and further, after the gap between the chest face of the patient 2 and the bottom face of the dewar 4 is adjusted with reference to the light beams 202, the bed 3 is displaced to the measurement position immediately below the dewar 4, thereby, a dangerous erroneous manipulation catching the patient strongly between the bed 3 and the dewar 4 due to an excess elevation of the bed 3 can be prevented. Moreover, since this gap adjustment controls and supplements the elevation unit 13 in such a manner that the elevation of the bed 3 is stopped by detecting an interruption of the light beams 202 by the patient 2, a position matching manipulation to an optimum gap is facilitated. When disposing such as the photoelectric switch 200, the indication lamp 204 and the buzzer 205 which generate magnetic fluxes during operation thereof near the dewar 4 (the magnetism sensors), it is possible that these magnetic fluxes cause adverse effect on the magnetism sensors as noises, therefore, these elements are disposed all together at the measurement preparation position remote from the dewar 4 (are disposed all together on the detection stand 203 provided along the wall side of the magnetically shielded room 1 at the opposite side of the dewar 4), thereby influences of these elements as noise sources are prevented.

In order to alarm when the patient 2 moves and the chest thereof is raised during the advancement or the measurement, abnormal detection use light beams are passed above the light beams 202 to detect the abnormal rise through interruption of the abnormality detection use light beams or alternatively the bed 3 is placed in the following condition, in that after elevating the bed 3 until the patient 2 interrupts the light beams 202 at the measurement preparation position and stopping the same, the interruption of the light beams 202 is released by opening the relief valve 18 and lowering the bed 3 slightly so that the photoelectric switch 200 outputs the patient non-detecting signals. When performing the advancing and retreating displacement and the measurement while keeping the height of the bed 3 under the above condition, an elevation of the chest thereafter, which interrupts the light beams 202 due to the movement of the patient 2, is detected based on the output signal of the photoelectric switch 200 and is alarmed through the indication lamp 204 or the buzzer 205.

In the above embodiments, with the microswitch 206 it is detected that the traveling stand 12 (bed 3) is positioned at the measurement preparation position and the control function which only permits the elevation of the bed 3 by the elevation unit 13 at the measurement preparation position is included, however, such control function can be omitted.

Still further, in the above embodiments the bed elevation mechanism and the bed right and left displacement mechanism are exemplified, however, according to the present invention a dewar elevation mechanism and/or a dewar right and left displacement mechanism can be of course introduced, in such instance, when a mechanism for elevating the light beams 202 in correlation with the dewar elevation is provided, the above explained present invention can be applied.

Hitherto, the cardio magnetism measurement devices have been explained as examples, however, the present invention can be commonly applied to a variety of biomagnetism measurement devices including a cerebral magnetism measurement device. In such cerebral magnetism measurement device, since the measurement plane includes a helmet shaped side face which at a first glace seems different from the flat shaped measurement plane according to the above embodiments, however, when performing the position detection of the measurement plane end portion with the light beams and when the constant distance transferring after the positioning is to be performed, the present invention is likely applied.

What is claimed is:

1. A biomagnetism measurement device comprising magnetism sensors each including a super conducting quantum interference device; a dewar which incorporates the magnetism sensors and which is filled with a coolant so as to maintain the magnetism sensors in a super conducting state; and a patient supporting apparatus for supporting a patient, characterized in that the biomagnetism measurement device further comprises:

a first light projecting means for projecting a first light beam pattern which spreads only in a direction of an X axis of the dewar;

a second light projecting means for projecting a second light beam pattern which spreads only in a direction of a Y axis of the dewar; and a mechanism which causes to cross the first light beam pattern from the first light projecting means with the second light beam pattern from the second light projecting means to produce a cross-shaped light beam pattern, and to project the cross-shaped light beam pattern onto the supported patient.

2. A biomagnetism measurement device according to claim 1, further comprising:

a displacement means which displaces relatively at least one of the patient supporting apparatus and the dewar based on relative positions of the crossing point of the cross-shaped light beam pattern and of the dewar.

3. A biomagnetism measurement device according to claim 1, wherein the first light projecting means projects the first light beam pattern with a spreading angle $\alpha$ in the X axis direction of the dewar, and wherein the second light projecting means projects the second light beam pattern with a spreading angle $\alpha$ in the Y axis direction of the dewar.

4. A method of biomagnetism measurement using a biomagnetism measurement device comprising magnetism sensors each including a super conducting quantum interference device; a dewar which incorporates the magnetism sensors and which is filled with a coolant so as to maintain the magnetism sensors in a super conducting state; and a patient supporting apparatus for supporting a patient for inspection, characterized in that the method comprises the steps of:

arranging the patient supporting apparatus supporting the patient outside a position immediately below the dewar; projecting a cross-shaped light beam pattern onto a specified portion of the patient, using a first light projecting means for projecting a first light beam pattern which spreads only in a direction of an X axis of the dewar; a second light projecting means for projecting a second light beam pattern which spreads only in a direction of a Y axis of the dewar; and a mechanism which causes to cross the first light beam pattern from the first light projecting means with the second light beam pattern from the second light projecting means to produce the cross-shaped light beam pattern, to thereby project the cross-shaped light beam pattern onto the supported patient; and displacing relatively at least one of the patient supporting apparatus and the dewar based on relative positions of the crossing point of the cross-shaped light beam pattern and of the dewar.

5. A method of biomagnetism measurement according to claim 4, wherein the projecting step is performed such that the first light projecting means projects the first light beam pattern with a spreading angle α in the X axis direction of the dewar, and the second light projecting means projects the second light beam pattern with a spreading angle α in the Y axis direction of the dewar.

6. A method of biomagnetism measurement using a biomagnetism measurement device comprising magnetism sensors each including a super conducting quantum interference device; a dewar having first and second dewar marks provided thereon, which incorporates the magnetism sensors and which is filled with a coolant so as to maintain the magnetism sensors in a super conducting state; and a patient supporting apparatus for supporting a patient for inspection, characterized in that the method comprises the steps of:

arranging the patient supporting apparatus supporting the patient outside a position immediately below the dewar;

projecting first and second light beam patterns onto a specified portion of the patient, using a first light projecting means for projecting the first light beam pattern which spreads only in a direction of an X axis of the dewar; a second light projecting means for projecting a second light beam pattern which spreads only in a direction of a Y axis of the dewar; and a mechanism which causes to cross the first light beam pattern from the first light projecting means with the second light beam pattern from the second light projecting means; and displacing at least one of the patient supporting apparatus and the dewar so that the first and second dewar marks respectively match with the first and second light beam patterns.

7. A method of biomagnetism measurement according to claim 6, wherein the projecting step is performed such that the first light projecting means projects the first light beam pattern with a spreading angle α in the X axis direction of the dewar, and the second light projecting means projects the second light beam pattern with a spreading angle α in the Y axis direction of the dewar.

8. A method of biomagnetism measurement using a biomagnetism measurement device comprising magnetism sensors each including a super conducting quantum interference device; a dewar which incorporates the magnetism sensors and which is filled with a coolant so as to maintain the magnetism sensors in a super conducting state; and a patient supporting apparatus for supporting a patient for inspection, characterized in that the method comprises the steps of:

arranging the patient supporting apparatus supporting the patient outside a position immediately below the dewar;

providing at least two marks on the patient for specifying a measurement portion;

projecting a cross-shaped light beam pattern onto the at least two marks using a first light projecting means for projecting a first light beam pattern which spreads only in a direction of an X axis of the dewar; a second light projecting means for projecting a second light beam pattern which spreads only in a direction of a Y axis of the dewar; and a mechanism which causes to cross the first light beam pattern from the first light projecting means with the second light beam pattern from the second light projecting means to produce the cross-shaped light beam pattern, to thereby project the cross-shaped light beam pattern onto the supported patient; and displacing relatively at least one of the patient supporting apparatus and the dewar based on relative positions of the crossing point of the cross-shaped light beam pattern and of the dewar.

9. A method of biomagnetism measurement according to claim 9, characterized in that the marks are made of lead or cod-liver drop.

10. A method of biomagnetism measurement according to claim 8, characterized in that a position matching of biomagnetism measurement data obtained by the method is performed through a combined use of the biomagnetism measurement data measured by providing the at least two marks on the patient, and an X-ray photograph taken by providing the at least two marks on the patient or an MR imaging image taken by providing the at least two marks on the patient.

11. A method of biomagnetism measurement according to claim 8, wherein the projecting step is performed such that the first light projecting means projects the first light beam pattern with a spreading angle α in the X axis direction of the dewar, and the second light projecting means projects the second light beam pattern with a spreading angle α in the Y axis direction of the dewar.

12. A method of biomagnetism measurement using a biomagnetism measurement device comprising magnetism sensors each including a super conducting quantum interference device; a dewar having first and second dewar marks provided thereon, which incorporates the magnetism sensors and which is filled with a coolant so as to maintain the magnetism sensors in a super conducting state; and a patient supporting apparatus for supporting a patient for inspection, characterized in that the method comprises the steps of:

arranging the patient supporting apparatus supporting the patient outside a position immediately below the dewar;

providing at least two marks on the patient for specifying a measurement portion;

projecting first and second light beam patterns onto the at least two marks using a first light projecting means for projecting a first light beam pattern which spreads only in a direction of an X axis of the dewar; a second light projecting means for projecting a second light beam pattern which spreads only in a direction of a Y axis of the dewar; and a mechanism which causes to cross the first light beam pattern from the first light projecting means with the second light beam pattern from the second light projecting means to produce the cross-shaped light beam pattern, to thereby project the cross-shaped light beam pattern onto the supported patient; and displacing at least one of the patient supporting apparatus and the dewar so that the first and second beam patterns respectively match with the first and second dewar marks provided on the dewar.

13. A method of biomagnetism measurement according to claim 12, characterized in that the marks are made of lead or cod-liver drop.

14. A method of biomagnetism measurement according to claim 12, wherein the projecting step is performed such that the first light projecting means projects the first light beam pattern with a spreading angle α in the X axis direction of the dewar, and the second light projecting means projects the second light beam pattern with a spreading angle α in the Y axis direction of the dewar.

15. A biomagnetism measurement device comprising magnetism sensors each including a super conducting quantum interference device; a dewar which incorporates the magnetism sensors and is filled with a coolant so as to maintain the magnetism sensors in a super conducting state; and a patient supporting apparatus for supporting a patient for inspection, characterized in that the biomagnetism measurement device further comprises:

an output means for outputting light beams passing under the bottom face of the dewar with a predetermined constant distance thereto;

means for receiving the light beams; and an alarming means which alarms an interruption of the light beams.

16. A biomagnetism measurement device according to claim 15, characterized in that the predetermined constant distance is 1~50 mm.

17. A biomagnetism measurement device according to claim 15, characterized in that the biomagnetism measurement device further comprises a reflection means which reflects the light beams.

18. A biomagnetism measurement device according to claim 17, characterized in that when the patient supporting apparatus and the dewar are located at the measurement position, one of the patient supporting apparatus and the dewar is only displaced in such a manner that the distance between the patient supporting apparatus and the dewar increases.

19. A biomagnetism measurement device comprising magnetism sensors each including a super conducting quantum interference device; a dewar which incorporates the magnetism sensors and is filled with a coolant so as to maintain the magnetism sensors in a super conducting state; and a patient supporting apparatus for supporting a patient for inspection, characterized in that the biomagnetism measurement device further comprises:

an output means for outputting light beams passing under the bottom face of the dewar with a predetermined constant distance thereto; and means for receiving the light beams, wherein when the light beams to the light receiving means are interrupted, displacement at least one of the patient supporting apparatus and the dewar is stopped.

20. A biomagnetism measurement device according to claim 19 characterized in that the biomagnetism measurement device further comprises an alarm means which alarms interruption of the light beams.

21. A biomagnetism measurement device according to claim 19, characterized in that the predetermined constant distance is 1~50 mm.

22. A biomagnetism measurement device according to claim 19, characterized in that the biomagnetism measurement device further comprises a reflection means which reflects the light beams.

23. A biomagnetism measurement device comprising magnetism sensors each including a super conducting quantum interference device; and a dewar which incorporates the magnetism sensors and is filled with a coolant so as to maintain the magnetism sensors in a super conducting state; and a patient supporting apparatus for supporting a patient for inspection, characterized in that the biomagnetism measurement device further comprises:

a displacement means which displaces at least one of the patient supporting apparatus and the dewar between a measurement preparation position and a measurement position;

an output means which outputs light beams passing through the measurement preparation position and the measurement position under the bottom face of the dewar with a predetermined constant distance thereto; and means for receiving the light beams, wherein when the light beams received by the light receiving means are interrupted, displacement at least one of the patient supporting apparatus and the dewar is stopped.

24. A biomagnetism measurement device according to claim 23, characterized in that the predetermined constant distance is 1~50 mm.

25. A biomagnetism measurement device according to claim 23, characterized in that the biomagnetism measurement device further comprises a reflection means which reflects the light beams.

26. A biomagnetism measurement device according to claim 23, characterized in that the biomagnetism measurement device further comprises an alarm means which alarms interruption of the light beams.

27. A method of positioning a patient in a biomagnetism measurement device comprising magnetism sensors each including a super conducting quantum interference device; a dewar which incorporates the magnetism sensors and is filled with a coolant so as to maintain the magnetism sensors in a super conducting state; and a patient supporting apparatus for supporting a patient, characterized in that when light beams passing under the bottom face of the dewar with a predetermined constant distance are interrupted, the interruption of the light beams is alarmed.

28. A method of positioning a patient in a biomagnetism measurement device according to claim 27, characterized in that the predetermined constant distance is 1~50 mm.

29. A method of positioning a patient in a biomagnetism measurement device comprising magnetism sensors each including a super conducting quantum interference device; a dewar which incorporates the magnetism sensors and is filled with a coolant so as to maintain the magnetism sensors in a super conducting state; and a patient supporting apparatus for supporting a patient, characterized in that the patient is approached to the dewar by displacing at least one of the patient supporting apparatus and the dewar, and when light beams passing under the bottom face of the dewar with a predetermined constant distance thereto are interrupted, the displacement at least one of the patient supporting apparatus and the dewar is stopped.

30. A method of positioning a patient in a biomagnetism measurement device, according to claim 29, characterized in that the predetermined constant distance is 1~50 mm.

31. A method of positioning a patient in a biomagnetism measurement device comprising magnetism sensors each including a super conducting quantum interference device; a dewar which incorporates the magnetism sensors and is filled with a coolant so as to maintain the magnetism sensors in a super conducting state; and a patient supporting apparatus for supporting a patient for inspection, characterized in that the patient at a measurement preparation position arranged outside a position immediately below the dewar is approached to the dewar by displacing at least one of the patient supporting apparatus and the dewar, when light beams passing through the measurement preparation position and a measurement position under the bottom face of the dewar with a predetermined constant distance thereto are interrupted, the displacement of at least one of the patient supporting apparatus and the dewar is stopped, and through displacement of at least one of the patient laying apparatus and the dewar the patient is arranged at the measurement position immediately below the dewar.

32. A method of positioning a patient in a biomagnetism measurement device, according to claim 31, characterized in that the predetermined constant distance is 1~50 mm.

* * * * *